United States Patent
Crosby et al.

(10) Patent No.: US 10,471,268 B2
(45) Date of Patent: Nov. 12, 2019

(54) SYSTEMS AND METHODS FOR MONITORING MUSCLE REHABILITATION

(71) Applicant: MAINSTAY MEDICAL LIMITED, Swords, County Dublin (IE)

(72) Inventors: Peter A. Crosby, Blaine, MN (US); Kristen N. Jaax, Santa Clara, CA (US); Prashant B. Rawat, Blaine, MN (US)

(73) Assignee: Mainstay Medical Limited, Dublin (IE)

( * ) Notice: Subject to any disclaimer, the term of this patent is extended or adjusted under 35 U.S.C. 154(b) by 808 days.

(21) Appl. No.: 14/882,087

(22) Filed: Oct. 13, 2015

(65) Prior Publication Data

US 2016/0106994 A1    Apr. 21, 2016

Related U.S. Application Data

(60) Provisional application No. 62/064,924, filed on Oct. 16, 2014.

(51) Int. Cl.
*A61N 2/00* (2006.01)
*A61N 1/36* (2006.01)
(Continued)

(52) U.S. Cl.
CPC .......... *A61N 2/004* (2013.01); *A61B 5/04001* (2013.01); *A61B 5/0488* (2013.01);
(Continued)

(58) Field of Classification Search
CPC ................ A61N 2/004; A61N 1/36135; A61N 1/36071; A61N 1/36067; A61N 1/36003;
(Continued)

(56) References Cited

U.S. PATENT DOCUMENTS

| 3,077,884 A | 2/1963 | Batrow et al. |
| 3,416,534 A | 12/1968 | Quinn |

(Continued)

FOREIGN PATENT DOCUMENTS

| CN | 1211930 C | 7/2005 |
| CN | 101678203 A | 3/2010 |

(Continued)

OTHER PUBLICATIONS

Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.

(Continued)

*Primary Examiner* — Kaylee R Wilson
(74) *Attorney, Agent, or Firm* — Eversheds Sutherland (US) LLP; Christopher C. Bolten; Nicola A. Pisano

(57) ABSTRACT

System and method for rehabilitating a muscle and monitoring such rehabilitation are provided, the system including a user input receiver for receiving stimulation parameter inputs from a user, a stimulator for generating stimulations to be applied to a patient's body based on the stimulation parameter inputs, a signal receiver to receive, detect, and record a signal containing an evoked potential generated by the body in response to the stimulations, a signal processor for processing the recorded signal, for example, by amplifying, filtering, digitizing and temporal averaging the recorded signal, a trigger detector to alert the signal processor module when stimulations are generated to enable synchronization of the response signal with the stimulus for accurate temporal averaging, and an output display for (Continued)

providing data representative of the evoked potential to the user.

13 Claims, 9 Drawing Sheets

(51) Int. Cl.
*A61N 2/02* (2006.01)
*A61B 5/04* (2006.01)
*A61B 5/0488* (2006.01)
*A61B 5/00* (2006.01)
*A61N 1/05* (2006.01)
*A61N 1/372* (2006.01)

(52) U.S. Cl.
CPC ........ *A61B 5/4836* (2013.01); *A61N 1/36003* (2013.01); *A61N 1/36067* (2013.01); *A61N 1/36071* (2013.01); *A61N 1/36135* (2013.01); *A61N 1/36139* (2013.01); *A61N 2/02* (2013.01); *A61B 5/4519* (2013.01); *A61B 5/686* (2013.01); *A61B 2505/09* (2013.01); *A61B 2562/043* (2013.01); *A61N 1/0551* (2013.01); *A61N 1/37211* (2013.01); *A61N 2/006* (2013.01)

(58) Field of Classification Search
CPC .. A61N 1/36139; A61N 2/02; A61N 1/37211; A61N 1/0551; A61N 1/3605; A61B 5/4836; A61B 5/04001; A61B 5/0488; A61B 5/686; A61B 5/4519; A61B 5/1104
See application file for complete search history.

(56) References Cited

U.S. PATENT DOCUMENTS

| | | |
|---|---|---|
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | Leveen et al. |
| 4,528,984 A | 7/1985 | Morawetz et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A | 12/1993 | Pohndorf |
| 5,300,108 A | 4/1994 | Rebell et al. |
| 5,330,515 A | 7/1994 | Rutecki et al. |
| 5,376,108 A | 12/1994 | Collins et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A | 4/1998 | Brennen |
| 5,782,841 A | 7/1998 | Ritz et al. |
| 5,807,234 A | 9/1998 | Bui et al. |
| 5,873,900 A | 2/1999 | Maurer et al. |
| 5,916,172 A | 6/1999 | Hodges et al. |
| 5,957,968 A | 9/1999 | Belden et al. |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 * | 3/2009 | Buhlmann ........... A61B 5/1107 607/2 |
| 7,502,651 B2 | 3/2009 | Kim et al. |
| 7,515,971 B1 | 4/2009 | Doan |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,321,021 B2 | 11/2012 | Kisker et al. |
| 8,380,318 B2 | 2/2013 | Kishawi et al. |
| 8,391,966 B2 | 3/2013 | Luo et al. |
| 8,409,233 B1 | 4/2013 | Chinn et al. |
| 8,428,728 B2 | 4/2013 | Sachs |
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |

(56) References Cited

U.S. PATENT DOCUMENTS

| | | |
|---|---|---|
| 9,079,019 B2 | 7/2015 | Crosby et al. |
| 9,108,053 B2 | 8/2015 | Crosby et al. |
| 9,320,847 B2 | 4/2016 | Rooney et al. |
| 9,561,364 B2 | 2/2017 | Bondhus |
| 9,861,811 B2 | 1/2018 | Crosby et al. |
| 9,950,159 B2 | 4/2018 | Beck et al. |
| 9,999,763 B2 | 6/2018 | Shiroff et al. |
| 10,016,603 B2 | 7/2018 | Sachs et al. |
| 10,195,419 B2 | 2/2019 | Shiroff et al. |
| 2001/0053885 A1 | 12/2001 | Gielen et al. |
| 2002/0065543 A1 | 5/2002 | Gomperz et al. |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120328 A1 | 6/2003 | Jenkins et al. |
| 2003/0135120 A1* | 7/2003 | Parks ............... A61B 5/037 600/463 |
| 2003/0199938 A1 | 10/2003 | Smits et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0070971 A1* | 3/2005 | Fowler ............ A61N 1/36082 607/45 |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1* | 7/2006 | Tehrani ............ A61B 5/0488 607/42 |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0105700 A1 | 4/2009 | Anderson |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0224665 A1* | 9/2011 | Crosby ............. A61B 18/1492 606/33 |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1* | 2/2013 | Hincapie Ordonez ..................... A61B 5/4035 607/62 |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |

(56) References Cited

U.S. PATENT DOCUMENTS

| | | |
|---|---|---|
| 2013/0238066 A1 | 9/2013 | Boggs et al. |
| 2013/0245715 A1 | 9/2013 | Peterson |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0031837 A1 | 1/2014 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0463998 | 2/2014 | Sachs Dan |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |
| 2017/0100408 A1 | 4/2017 | Bertolini et al. |
| 2018/0008311 A1 | 1/2018 | Shiroff et al. |

FOREIGN PATENT DOCUMENTS

| | | |
|---|---|---|
| EP | 0 587 269 B1 | 12/1998 |
| EP | 1 053 762 B1 | 11/2000 |
| EP | 1 255 583 A1 | 11/2002 |
| EP | 2 125 100 A1 | 12/2009 |
| EP | 2 273 931 A1 | 1/2011 |
| WO | WO-01/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO-2006/133445 A3 | 12/2006 |
| WO | WO-2006/135791 A2 | 12/2006 |
| WO | WO-2007/051146 A1 | 5/2007 |
| WO | WO-2007/138598 A2 | 12/2007 |
| WO | WO-2008/048471 A2 | 4/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A2 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013/138786 A1 | 9/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |
| WO | WO-2018/007914 A1 | 1/2018 |

OTHER PUBLICATIONS

Baker et al., "Clinical Uses of Neuromuscular Electrical Stimulation," NeuroMuscular Electrical Stimulation—A Practical Guide, 4th ed. Rancho Los Amigos Research and Education Institute Inc., pp. 47-66 (2000).

Bhadra et al., "Peripheral nerve stimulation for restoration of motor function," Journal of Clinical Neurophysiology: Official Publication of the American Electroencephalographic Society, 14(5):378-33 (Sep. 1997).

Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).

Bowman et al., "Effects of Waveform Parameters on Comfort during Transcutaneous Neuromuscular Electrical Stimulation," Annals of Biomedical Engineering, 13:59-74 (1985).

Bradford et al., "Surface Electrical Stimulation in the Treatment of Idiopathic Scoliosis: Preliminary Results in 30 Patients," Spine, 8(7):757-764 (1983).

Brazier et al., "A Comparison of the EQ-5D and SF-6D Across Seven Patient Groups," Health Economics, 13:873-884 (2004).

Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.

Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.

Crago et al., "The choice of pulse duration for chronic electrical stimulation via surface, nerve, and intramuscular electrodes," Annals of Biomedical Engineering, 2(3):252-264 (1974).

Criterion Inc., "NMES Treatment Protocols," 3 pages (accessed Jun. 7, 2012) available at http://www.criterionmed.com/PDF/NMES%20Treatment%20Protocols.pdf.

Durham et al., "Surface Electrical Stimulation Versus Brace in Treatment of Idiopathic Scoliosis," Spine, 15(9):888-891 (1990).

EMPI, "Low Back Syndrome/Chronic Low Back Pain," NMES Guidelines for Treatment, 2 pages (2003).

Extended European Search Report dated Mar. 5, 2015 in EP Patent Appl Serial No. 14189412.1.

Extended European Search Report dated Jan. 7, 2013 in European Patent Application No. 12176863.

Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.

Freeman, et al., The Role of the Lumbar Multifidus in Chronic Low Back Pain: A Review, American Academy of Physical Medicine and Rehabilitation, 2:142-146 (2010).

Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).

Garmirian, et al., Discriminating Neurogenic from Myopathic Disease via Measurement of Muscle Anisotrophy, Muscle Nerve, 39(1):16-24 (2009) (Abstract only).

Gazelle et al., "Tumor Ablation with radio-frequency Energy," Radiology, (2000), 217(3):633-646.

Glaser et al., "Electrical Muscle Stimulation as an Adjunct to Exercise Therapy in the Treatment of Nonacute Low Back Pain: A Randomized Trial," The Journal of Pain, 2(5):295-300 (2001).

Gorman et al., "The effect of stimulus parameters on the recruitment characteristics of direct nerve stimulation," IEEE Transactions on Bio-medical Engineering, 30(7):407-414 (1983).

Haemmerich et al., "Thermal Tumor Ablation: Devices, Clinical Applications and Future Directions," Int. J. Hyperthermia, (2005) 21(8):775-760 (Abstract Only).

Hagg et al., "The Clinical Importance of Changes in Outcome Scores After Treatment for Chronic Low Back Pain," Eur. Spine. J., 12:12-20 (2003).

Herbert et al., "Scoliosis Treatment in Children Using a Programmable, Totally Implantable Muscle Stimulator (ESI)," IEEE Transactions on Biomedical Engineering, 36(7):801 (Jul. 1989).

Hodges et al., "Response of the deep paraspinal muscles to cortical but not transmastoid stimulation is increased at a single lumbar level following interverebral disc lesion," Progress in Motor Control Vi—Brazil. 36:2-3 (2007).

(56) References Cited

OTHER PUBLICATIONS

Hodges, et al., Intervetebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Informal Response to Written Opinion dated Jan. 17, 2012 in Int'l PCT Patent Appl. Serial No. PCT/US2011/027834.
International Search Report & Written Opinion dated Jan. 19, 2016 in Int'l PCT Patent Appl. Serial No. PCT/IB2015/055926.
International Search Report & Written Opinion dated Mar. 19, 2015 in Int'l PCT Patent Appln Serial No. PCT/IB2014/002920.
International Search Report & Written Opinion dated Apr. 5, 2013 in Int'l PCT Patent Application Serial No. PCT/US2012/070259.
International Search Report & Written Opinion dated Jun. 25, 2008 in Int'l PCT Patent Appl No. PCT/US08/03126.
International Search Report and Written Opinion dated Oct. 16, 2015 in Int'l PCT Patent Appl Serial No. PCT/US2015/032732.
International Search Report dated Oct. 19, 2011 in Int'l PCT Patent Appl. Serial No. PCT/US2011/027934.
International Search Report and Written Opinion dated Jan. 26, 2016 in Int'l PCT Patent Appl. Serial No. PCT/IB2015/057838.
Keller, et al., Muscular Contributions to Dynamic Dorsoventral Lumber Spine Stiffness, Eur. Spine J., 16(2):245-54 (2007).
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Miyatani, et al., Validity of Estimating Limb Muscle Volume by Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/10.1111/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Appl Serial No. PCT/US2015/032732.
PCT International Search Report and Written Opinion dated Sep. 3, 2013 in related PCT Application No. PCT/US2013/045223.
PCT Written Opinion dated Aug. 23, 2013 in Int'l PCT Application No. PCT/US2010/049148.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.1ww.com/pedpt/pages/articleviewer.aspx?year=1997&issue=00930&article=00002&type=abstract.
RS Medical, "RS-4M Muscle Stimulator," available at Http://www.rsmedical.com/documents/fact_sheet_RS4m.pdf (last visited Jul. 19, 2012).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Sippl, Charles J., "Computer Dictionary: Third Edition," pp. 2257 and 340.
Sluijter, "Radiofrequency Ablation in the Management of Spinal Pain," C212, (2006), IV(1):10-15.
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.
Stokes, et al., "Surface EMG Electrodes Do Not Accurately Record from Lumbar Multifidus Muscles," Clin. Biomech, (2003), 18(1):9-13 (Abstract Only).
Van Dieen, et al., "Trunk Muscle Recruitment Patterns," Spine, (2003), 28(8):834-841 (Abstract Only).
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Van Zundert et al., "Radiofrequency treatment for chronic pain syndromes," CPD Anaesthesis, 6(1):13-17 (2004).
Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.
Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).

(56) References Cited

OTHER PUBLICATIONS

Wikipedia, "Interference Fit," http://en.wikipedia.org/wiki/Interference_fit, accessed Dec. 4, 2014.
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
Written Opinion dated Nov. 16, 2011 in Int'l PCT Patent Appl. Serial No. PCT/US2011/027934.
Gondin, et al., Electromyostimulation training effects on neural drive and muscle architecture, Med. Sci. Sports. Exerc., 37(8):1291-9 (2005).
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Rosatelli, et al., Three-dimensional study of the musculotendinous architecture of lumbar multifidus and its functional implications, Clinical Anatomy 21(6):539-44 (2008).
Deckers, et al., Chronic Low Back Pain: Restoration of Dynamic Stability, Neuromodulation, 18:478-486 (2015).
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
MicroProbes for Life Science, Nerve Cuff electrodes, 2018, available at https://microprobes.com/products/peripheral-electrodes/nerve-cuff, accessed Mar. 5, 2018.
Unit III—The Spine, "Motions of the Spine," available at https://courses.vcu.edu/DANC291-003/unit_3.htm, accessed Mar. 5, 2018.
Wikipedia, "Anterior superior iliac spine," Updated Feb. 12, 2018, available at https://en.wikipedia.org/wiki/Anterior_superior_iliac_spine.
Wikipedia, "Blunt Dissection," Updated Feb. 14, 2018, available at https://en.wikipedia.org/wiki/Blunt_dissection.
Wikipedia, "Cavernous nerves," Updated Feb. 26, 2018, available at https://en.wikipedia.org/wiki/Cavernous_nerves.
Wikipedia, "Dorsal ramus of spinal nerve," Updated Feb. 12, 2018, available at https://en.wikipedia.org/wiki/Dorsal_ramus_of_spinal_nerve.
Wikipedia, "Ventral ramus of spinal nerve," Updated Feb. 12, 2018, available at https://en.wikipedia.org/wiki/Ventral_ramus_of_spinal_nerve.
Russo, M.D., et al., Muscle Control and Non-specific Chronic Low Back Pain, Neuromodulation: Technology at the Neural Interface, 21:1-9 (2017).

\* cited by examiner

SYSTEMS AND METHODS FOR MONITORING MUSCLE REHABILITATION

I. CROSS-REFERENCE TO RELATED APPLICATIONS

This application claims the benefit of priority of U.S. Provisional Patent Application No. 62/064,924, filed Oct. 16, 2014, the entire contents of which are incorporated herein by reference.

II. FIELD OF THE INVENTION

This application generally relates to assessment of the physiological state of a muscle subject to therapeutic stimulation. In particular, this application is directed to a system and method for monitoring progress of muscular rehabilitation.

III. BACKGROUND OF THE INVENTION

Back pain in the lower, or lumbar, region of the back is common. In many cases, the cause of back pain is unknown. The human back is a complicated structure including bones, muscles, ligaments, tendons, nerves and other structures, which together form the spinal stabilization system. The spinal stabilization system may be conceptualized to include three subsystems: 1) the spinal column, which provides intrinsic mechanical stability; 2) the spinal muscles, which surround the spinal column and provide dynamic mechanical stability; and 3) the neuromotor control unit, which evaluates and determines requirements for stability via a coordinated muscle response. In a properly functioning system, neuromotor control unit sensors present in the connective tissue of the spinal column and the muscle spindles of the spinal muscles each transmit signals via nerves to the motor cortex of the brain to provide information such as the force a muscle is exerting or the position of a joint. The motor cortex uses signals from the body's neuromotor control unit sensors to form a sense of the body's position in space. This sense is referred to as proprioception. The motor cortex of the brain returns signals to the spinal muscles to control the spine's position in space. Thus, in patients with a functional stabilization system, the three subsystems work together to form a feedback loop that provides mechanical stability to the spine. It is applicant's realization that lower back pain often results from dysfunction of these subsystems and disruption of the feedback loop.

Some cases of back pain are caused by abnormal mechanics of the spinal column. The spinal column consists of vertebrae and ligaments, e.g. spinal ligaments, disc annulus, and facet capsules. Degenerative changes to these structures, injury of the ligaments, acute trauma, or repetitive microtrauma may lead to back pain via inflammation, biochemical and nutritional changes, immunological factors, changes in the structure or material of the endplates or discs, and pathology of neural structures.

It is believed that in some patients with back pain, the spinal stabilization system is dysfunctional. Under normal circumstances, mechanoreceptors present in the ligaments, facet capsules, disc annulus, and other connective tissues generate signals describing spinal posture, motions, and loads. These signals provide information to the neuromuscular control unit, which generates muscle response patterns to activate and coordinate the spinal muscles to provide dynamic mechanical stability. The neuromuscular control unit produces a muscle response pattern based upon several factors, including the need for spinal stability, postural control, balance, and stress reduction on various spinal components. If the spinal column structure is compromised, for example, due to injury, degeneration, or viscoelastic creep, then muscular stability must be adjusted to compensate and maintain spinal stability. However, ligament injury, soft tissue fatigue, viscoelastic creep, and other connective tissue injuries may cause mechanoreceptors to produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Moreover, muscles may disrupt the spinal stabilization system by going into spasm, contracting when they should remain inactive, developing trigger points, or contracting out of sequence with other muscles. Such muscle dysfunction may cause muscle spindle mechanoreceptors to send abnormal signals to the motor cortex, which further may compromise normal muscle activation patterns via the feedback loops.

Through such mechanisms, disruptions to the spinal stabilization system can result in spine instability, which can lead to low back pain. In particular, spine instability can result in the generation of high loads on spinal structures when the spine moves beyond its neutral zone. The neutral zone is a range of intervertebral motion, measured from a neutral position, within which spinal motion is produced with a minimal internal resistance. High loads can lead to inflammation, disc degeneration, facet joint degeneration, and muscle fatigue. Since the endplates and annulus have a rich nerve supply, it is believed that abnormally high loads on such structures, resulting from spine instability, may be a common cause of pain. Load transmission to the facet joints also may increase with degenerative disc disease, leading to facet arthritis and facet joint pain.

A need exists for improving spine stability in many patients suffering from lower back pain. It is applicant's hypothesis that repetitive and episodic contraction of the local muscle system of the back may generate afferent signals to the brain capable of reactivating or awakening the spinal stabilization system, thereby stabilizing the spine and reducing pain.

The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments, is an example of a muscle of the local muscle system.

The multifidus is the largest and most medial of the lumbar back muscles. It has a complex structure with repeating series of fascicles stemming from the laminae and spinous processes of the vertebrae, which exhibit a consistent pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles that attach to the mamillary processes attach to the capsules of the facet joints next to the mamillary processes. The fascicles arriving from the spinous process of a given vertebra are innervated by the medial branch of the dorsal ramus nerve that issues from below that vertebra.

The lumbar multifidus and other skeletal muscles consist of a number of specialized elongated cells mechanically coupled together. A nerve fiber connects to the muscle cells at a region called the end plate. The combination of the muscle cell or group of cells and the nerve fiber that innervates it is called a motor unit. Motor units come in different sizes, with larger motor units producing greater force than smaller motor units given equal stimulation. An electrical signal transmitted to a nerve will travel down the nerve fiber and cause depolarization of the cell wall of the muscle fiber, thereby triggering biochemical processes inside the muscle cell that generate a twitch of contraction and resultant force generation.

Nerves to skeletal muscles generally include a mix of motor nerves and sensory nerves. Motor nerves are efferent nerves, which carry electrical signals from the brain to cause an action in a muscle, and sensory nerves are afferent nerves, carrying signals from remote structures to the brain to provide information to the brain.

External electrical stimulation for causing muscle contraction has been known since Galvani observed such contraction in frogs in 1791. Over time, it became known that the most energy efficient way to apply electrical stimulation to cause a muscle contraction is to stimulate the nerve fiber of the motor unit because the energy required to stimulate a nerve fiber to elicit contraction is about 1000 times less than required to stimulate a muscle to elicit contraction.

If an electrical stimulation electrode is placed on or adjacent to the nerve that supplies the muscle, then a single electrical pulse will cause a single contraction of the muscle referred to as a twitch. The force in the muscle rises rapidly and decays more slowly to zero. The amount of muscle that contracts, and hence, the force of contraction, in the twitch is determined primarily by the number of motor units stimulated.

If additional stimulation pulses are applied, additional twitches are produced. If the rate of stimulation is such that a new stimulation pulse is presented before the prior twitch has decayed, then the new twitch will be largely superimposed on the prior, producing a summation of force. As the stimulation rate is increased, this summation of force is such that the twitches blend together to generate a smooth contraction. The stimulation frequency at which the force production transitions from intermittent (rapid twitching) to smooth contraction is often referred to as the fusion frequency. Stimulation at a rate at or above the fusion frequency leads to smooth force generation. In general terms, stimulation at a rate significantly higher than the fusion frequency has minimal effect on the strength or nature of contraction and may, in fact, have an adverse impact on fatigue of the muscle. Stimulation at a frequency higher than necessary to achieve the desired (e.g., maximum) force is energy inefficient, which is an important consideration for an implantable device.

Functional electrical stimulation (FES) is the application of electrical stimulation to cause muscle contraction to re-animate limbs following damage to the nervous system such as with stroke or spinal cord injury. FES has been the subject of much prior art and scientific publications. In FES, the goal generally is to bypass the damaged nervous system and provide electrical stimulation to nerves or muscles directly, which simulates the action of the nervous system. One lofty goal of FES is to enable paralyzed people to walk again, and that requires the coordinated action of many muscles activating several joints. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

Neuromuscular Electrical Stimulation (NMES) is a subset of the general field of electrical stimulation for muscle contraction, as it is generally applied to nerves and muscles which are anatomically intact but malfunctioning in a different way. NMES may be delivered via an external system or, in some applications, via an implanted system.

NMES via externally applied skin electrodes has been used to rehabilitate skeletal muscles after injury or surgery to an associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

An implanted NMES system has been used to treat incontinence by stimulating nerves that supply the urinary or anal sphincter muscles. For example, U.S. Pat. No. 5,199,430 to Fang describes an implantable electronic apparatus for assisting the urinary sphincter to relax.

For rehabilitation of anatomically intact (i.e., functionally disordered) neuromuscular systems, the primary goal is to restore normal functioning of the neuromuscular system. One application for an implanted NMES system is to restore normal functioning of the spinal stabilization system in order to improve spine stability in patients suffering from lower back pain. Such an application is described in U.S. Pat. Nos. 8,428,728 and 8,606,358 to Sachs and U.S. Application Publication No. 2011/0224665 to Crosby, each of which is incorporated herein by reference in its entirety. These references describe implanted electrical stimulation devices designed to restore neural drive and rehabilitate local muscles of the back, such as the multifidus muscle, to improve stability of the spine. It is theorized here that providing appropriate electrical stimulations to the multifidus muscle using an implanted NMES system to generate repetitive and episodic contractions of the multifidus muscle may reactivate the feedback loop and spinal stabilization system over time.

Another form of stimulation therapy is trans-cranial magnetic stimulation (TMS), which also may be used to activate skeletal muscles. In TMS, a time varying magnetic field is generated to induce an electrical current. Applying such a magnetic field with a coil positioned over a patient's skull can induce an electrical current in the patient's brain tissue. This technique has been used to stimulate portions of the motor cortex by applying and focusing a magnetic field over certain regions of the brain, primarily in the motor cortex. A patient's response to TMS pulses can be observed as a muscle twitch or as an electrical signal such as an electromyogram (EMG). TMS has been used to reactivate the quadriceps muscle following loss of volitional quadriceps activation resulting from meniscectomy.

One of the challenges of stimulation therapies such as NMES and TMS is monitoring to ensure the stimulation device is positioned properly, applying appropriate levels of stimulation, and resulting in a positive therapeutic effect. Monitoring can be especially challenging for deep muscles such as the deep fascicles of the lumbar multifidus, which are too deeply positioned for contractions to be reliably observed visually. A related challenge of NMES and TMS for rehabilitation of skeletal muscles is to diagnose when the therapy has been successful and may be discontinued. This is particularly important with patients who cannot communicate, e.g., young children, or patients who do not want to communicate, e.g., malingerers who may be motivated for the therapy to not be successful as it would result in loss of worker's compensation insurance.

It would therefore be desirable to provide a system and method to objectively monitor progress and diagnose when stimulation therapy of a skeletal muscle has been successful. To further research and the development of future therapies, it would also be desirable to provide a system and method that enable mapping at the various areas of the motor cortex and enable generation and display of motor cortex representations of the muscles. Accordingly, it would be advantageous to provide a system and method that enable controlled monitoring of muscle responses resulting from various motor cortex stimulations. Such muscle responses may result in recordable signals, such as evoked potentials.

An evoked potential is an electrical signal recorded from a part of the body, which results from the presentation of a stimulus to a portion of the body. Evoked potentials include, for example, somatosensory evoked potentials (SSEPs), visual evoked potentials (VEPs), motor evoked potentials (MEPs), and brain stem auditory evoked potentials (BAEPs). SSEPs consist of a series of electrical waves that reflect sequential activation of neural structures in the somatosensory pathways. SSEPs can be measured at the cortex of the brain or at various sites along the somatosensory pathway, including at peripheral nerves. SSEPs can be triggered with electrical stimulation along the somatosensory pathway, for example, at a peripheral nerve. SSEPs can also be triggered by mechanical stimulation near a peripheral nerve.

Evoked potentials are currently used as a measure of nerve functionality in some clinical procedures. Current clinical uses of evoked potential testing include measuring nerve signal conduction velocity, which can be an important diagnostic tool for diseases of the nervous system, such as multiple sclerosis, and verifying spinal cord functioning during spine surgery, as described in U.S. Pat. No. 8,016,846 to McFarlin et al. and U.S. Pat. No. 7,981,144 to Geist et al. Evoked potentials can also be used on a temporary basis as an aid to placing electrodes in or near the nervous system, for example, at the dorsal root ganglion, as described in U.S. Pat. No. 7,337,006 to Kim et al. A variety of techniques have been developed for the analysis of evoked potentials, for example, the techniques described in U.S. Pat. No. 8,391,966 to Luo et al., U.S. Pat. No. 5,638,825 to Fukuzumi et al., and U.S. Pat. No. 8,498,697 to Yong et al.

Compared to other biological signals, many types of evoked potentials are quite small. Often, in clinical situations, the small size of an evoked potential is not visible in the raw data when a single stimulus is applied. To extract the electrical signal of interest from the background noise, the technique of signal averaging is employed. Signal averaging can be spatial, temporal, or some combination (i.e., spatio-temporal averaging). In spatial averaging, a mathematical combination of signals are collected over a region of space in response to a stimulus. In temporal averaging, a mathematical combination of signals are synchronized in time in response to a stimulus. With temporal averaging, the electrical signals recorded following the stimulus are sampled using an analog-to-digital converter, then the time series of the samples is added together and divided by the number of samples to preserve scaling. The time series is synchronized with the stimulus event. In this manner, the background signal, which is asynchronous to the stimulus, tends towards its mean of zero, and the evoked potential average tends to a useful value above the background noise. The signal-to-noise ratio improves with the square root of the number of responses that are averaged. As will be appreciated by one skilled in the art, the specific combination of filtering parameters, sampling frequency, and number of scans to be averaged is determined by the nature of the evoked potential to be measured.

In the description provided herein, the term "evoked potentials" refers to electrical signals. There are other "evoked response" signals generated in response to a stimulus, such as force generation or movement of a muscle in response to electrical stimulation and motion of the eyes (saccade) in response to a visual stimulus.

It would be desirable to provide a system or method to detect and measure evoked potentials and other evoked responses to objectively monitor progress, optimize treatment, and diagnose when rehabilitation of a skeletal muscle has been attained.

It would be desirable to provide a system or method for monitoring and recording progress of NMES or TMS for rehabilitation of the lumbar multifidus muscle.

It further would be desirable to provide a system or method that provides data needed to adjust the operating parameters of an NMES or TMS system based on measurements of muscle performance, thereby continually optimizing the stimulation system.

It would also be desirable to monitor the effects of a stimulation system on a tissue's electrical activity, for example, to confirm applicant's hypothesis that repetitive and episodic contraction of the local muscle system of the back generates afferent signals to the brain capable of reactivating or awakening the spinal stabilization system. It would thus be desirable to provide a system and/or method capable of detecting and recording signals generated by a patient's body in response to repetitive and episodic stimulations to, and contraction of, the local muscle system of the back.

IV. SUMMARY OF THE INVENTION

The present invention overcomes the drawbacks of previously-known systems by providing systems and methods for measuring a body's response to stimulations to objectively monitor progress of, and make informed adjustments to, a stimulation rehabilitation protocol.

The stimulation monitoring system includes: a user input receiver module configured to receive stimulation parameter inputs from a user; and an optional stimulation activator module configured to transmit the inputs received from the user to a stimulator module. The stimulator module may be configured to generate stimulations to be applied to a patient's body based on the stimulation parameter inputs. The system further may include: a signal receiver module configured to receive, detect, and record a response signal generated by the body in response to the stimulations; a signal processor module configured to process the recorded response signal, for example, by amplifying, filtering, digitizing and temporal averaging the recorded signal; a trigger detector module configured to alert the signal processor module when stimulations are generated to enable synchronization of the response signal with the stimulus for accurate temporal averaging; and a graphical user interface configured to provide data representative of the response signal to the user.

In accordance with one aspect of the present invention, a method for monitoring rehabilitation of a muscle is provided. The method may include: receiving from an extracorporeal source a first input defining a first stimulation protocol, wherein the first stimulation protocol includes a plurality of parameters for generation of an electric current or a voltage; automatically applying the first stimulation protocol to a portion of a patient's body to cause contraction of a skeletal target muscle associated with control of the lumbar spine; automatically recording a response signal generated by the patient's body in response to the first stimulation protocol; automatically processing the recorded response signal to produce a processed signal; automatically displaying information indicative of the processed signal; receiving a second input from the extracorporeal source to adjust the first stimulation protocol; and automatically applying an adjusted stimulation protocol to the body portion to cause contraction of the skeletal target muscle.

The first input may be entered by a clinician and may specify one or more parameters of the first stimulation protocol. Such parameters may be selected from parameters such as pulse amplitude, pulse width, stimulation rate, stimulation frequency, ramp timing, cycle timing, session timing, duty cycle, contacts activated, percent of current allocated to each contact, and location of stimulation.

The target muscle may be weak, injured, or malfunctioning. In one embodiment, the target muscle is the lumbar multifidus. In another embodiment, the target muscle is at least one of the lumbar multifidus, the transverse abdominus, the erector spinae, the iliocostalis, or the longissimus. The portion of the patient's body to which the first stimulation protocol is applied may be the medial branch of the dorsal ramus nerve, which innervates the lumbar multifidus.

The electric current or electric voltage of the first stimulation protocol may include a plurality of electrical pulses generated by an implanted neuromuscular electrical stimulation device, and the electrical pulses may be applied to the patient's body by a first implanted stimulating electrode.

The response signal may be at least one of an electrical signal, a force signal, or a movement signal. In one embodiment, the response signal is an evoked potential. The response signal may be recorded by a second implanted electrode (which may be a recording electrode or a stimulating and recording electrode), and the recorded response signal or the processed signal may be transmitted wirelessly to an external receiver. Alternatively, the response signal may be recorded by a surface electrode attached to the patient at the head, neck, spine or other part of the body, and the recorded response signal may be received by a processor from the surface electrode via a wired or wireless connection. In another alternate embodiment, the electric current may be generated by a trans-cranial magnetic stimulation device and applied to the patient's skull by an inductive coil, and the response signal may be recorded by an implanted recording electrode implanted on, in, or near the deep skeletal target tissue, and the recorded response signal or the processed signal may be transmitted wirelessly to an external receiver.

Processing the recorded response signal may include amplifying the recorded response signal, filtering the recorded response signal, digitizing the recorded response signal, and/or taking a temporal average of the recorded response signal, if the recorded response signal is an electrical signal. In an embodiment in which the recorded response signal is temporally averaged, the method further may include generating a trigger signal upon initiating application of the first stimulation protocol and synchronizing the recorded response signal with the trigger signal.

Information indicative of the processed signal may be displayed on a computer monitor or other display screen. Such information may include a waveform of the processed signal. Additionally or alternatively, the displayed information may include one or more quantitative metrics of the processed signal, such as: amplitude, width, frequency, latency relative to application of the first stimulation protocol, and/or slope.

The method further may include recording a second response signal generated in response to the adjusted stimulation protocol, processing the second response signal to produce a second processed signal, and displaying information indicative of the second processed signal.

In accordance with another aspect of the present invention, a feedback loop system for monitoring rehabilitation of a muscle is provided. The system may include: a user interface configured to receive a first input from a user defining a stimulation protocol comprising a plurality of parameters for generation of an electric current; a transcranial magnetic stimulation device communicatively coupled to the user interface to receive the stimulation protocol, the transcranial magnetic stimulation device comprising an inductive coil positionable over a patient's skull and configured to generate an electromagnetic field in accordance with the stimulation protocol; an implantable device comprising a recording electrode and a processor configured to receive, detect, and record a response signal generated by the body in response to the stimulation protocol; a trigger detector communicatively coupled to the transcranial magnetic stimulation device and configured to transmit a wireless signal to the implantable device upon application of the stimulation protocol; an external receiver comprising an electromagnetic or radiofrequency telemetry unit wirelessly coupled to the implantable device and configured to receive the response signal from the implantable device; and an output display having a screen configured to display data representative of the response signal.

The trigger detector may include an electromagnetic or radiofrequency telemetry unit. The inductive loop of the transcranial magnetic stimulation device may be housed within a helmet or other unit adjacent to or contacting the head. The user interface and the output display may be integrated into a common device. Similarly, the trigger detector and the external receiver may be integrated into a common device.

V. BRIEF DESCRIPTION OF THE DRAWINGS

FIGS. 1A and 1B each depicts a functional block diagram representing functional features of an exemplary embodiment of a stimulation monitoring system constructed in accordance with the principles of the present invention.

FIG. 2A depicts a generalized block diagram of an exemplary embodiment of a stimulation monitoring system constructed in accordance with the principles of the present invention. In the depicted system, an implantable NMES device generates stimulation pulses and further records response signals.

FIGS. 2B and 2C depict alternative generalized block diagrams of the stimulation monitoring system of FIG. 2A, wherein the system of FIG. 2B has externally placed recording electrodes and an externally located device for recording response signals, and the system of FIG. 2C has an externally located TMS device generating stimulations and an implantable recording device recording the response signals.

VI. DETAILED DESCRIPTION OF THE INVENTION

A system and a method for monitoring stimulation therapy of skeletal muscles are described herein. Increasingly, neuromuscular electrical stimulation (NMES) and trans-cranial magnetic stimulation (TMS) are being utilized to treat and rehabilitate muscles. It is believed that such therapies may achieve positive outcomes by improving the functionality of feedback loops between muscles and the nervous system controlling them. NMES may be applied to a patient through an implanted NMES apparatus, such as through the implantable pulse generator (IPG) described in U.S. Pat. Nos. 8,428,728 and 8,606,358 to Sachs and U.S. Application Publication No. 2011/0224665 to Crosby, each of which is incorporated by reference herein. Alternatively, TMS may be applied to a patient externally using electromagnetic coils positioned on or near a patient's skull. While it is known that such techniques deliver a stimulating electrical current or voltage to patients which results in muscle contraction that can lead to improved muscle function, it is difficult to monitor the precise physiological effects of such therapy. A feedback system is needed, which allows clinicians to monitor, objectively and quantitatively, the physiological changes that result from stimulation therapy.

Various embodiments described herein provide a feedback system that fills one or more of the needs described above. The system and related method disclosed herein may allow clinicians to quantitatively track changes in nerve functionality during and following stimulation therapy, thus allowing clinicians to track treatment progress and observe the effects of treatment adjustments. With such data, clinicians may be able to optimize muscle rehabilitation treatment.

Figure 1A:
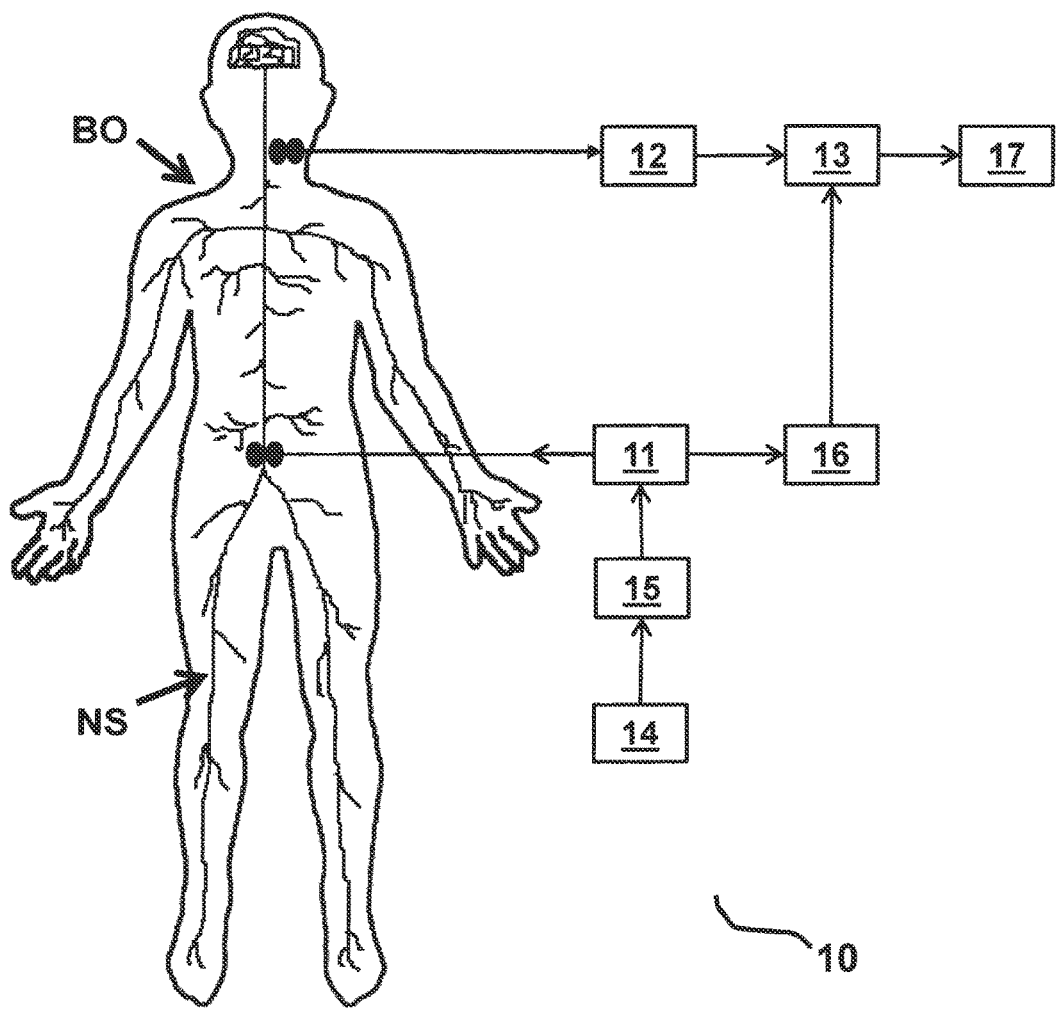
Figure 1B:
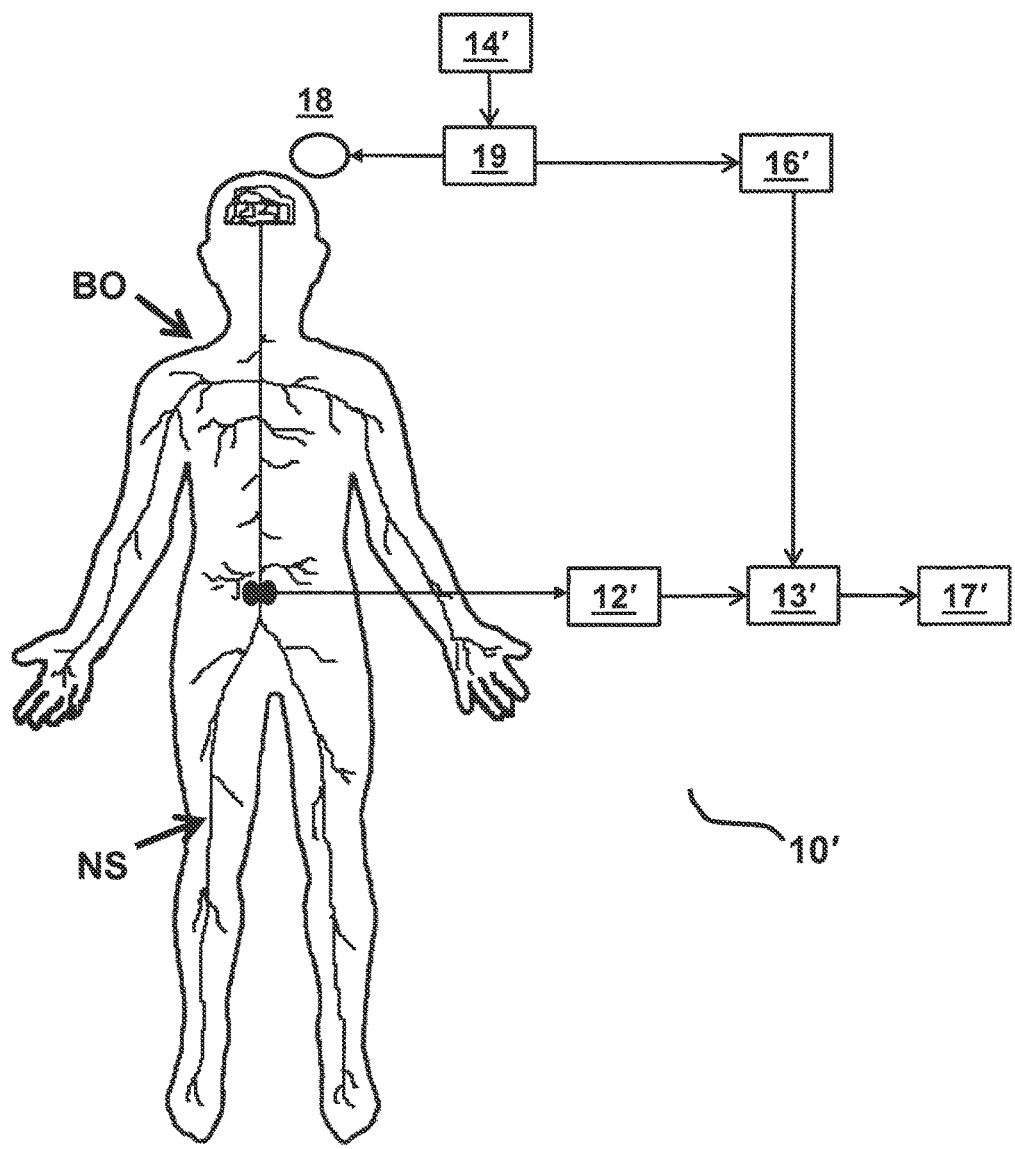

Referring to FIGS. 1A and 1B, an overview of exemplary stimulation monitoring systems constructed in accordance with the principles of the present invention is provided. Stimulation monitoring system 10' of FIG. 1B is constructed similarly to stimulation monitoring system 1 of FIG. 1A, wherein like components are identified by like primed reference numbers. In each embodiment, the system both generates a stimulus which may cause muscles to contract and provides a user with feedback on the effects of such stimulation. In FIGS. 1A and 1B, the system is described functionally with each block in the functional block diagram representing a different functional module of stimulation monitoring system 10 or 10'. System 10/10' each includes, at least, a stimulating means (e.g., either stimulator 11 or TMS system 18 and 19), signal receiver 12/12', and signal processor 13/13'. These modules together function to: present a stimulus to a portion of patient's body BO, and measure the evoked potential or other response signal generated by a portion of patient's nervous system NS in response.

In one embodiment, stimulator 11 is the source of electrical stimulus; it generates the stimulations to be applied to body BO of a patient. Stimulator 11 may be, for example, an implantable NMES device. In various embodiments, stimulator 11 delivers electrical signals to a stimulating electrode, stimulating coil, or other applicator configured and positioned to apply an electrical current or voltage to a portion of the patient. In an embodiment where stimulator 11 is configured to be implanted, stimulator 11 may include one or more electrodes coupled to an NMES device or implantable pulse generator (IPG), e.g., via a lead. The electrodes may be positioned to stimulate a peripheral nerve where the nerve enters skeletal muscle, which may be one or more of the multifidus, transverse abdominus, quadratus lumborum, psoas major, internus abdominus, obliquus externus abdominus, iliocostalis, longissimus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

In an alternative embodiment, the stimulus is applied via a TMS system, which includes coil 18 connected to TMS control unit 19. The TMS system generates magnetic fields which excite neurons in the motor cortex of the brain, thereby eliciting a signal which may cause muscle contraction analogous to the muscle contraction elicited by electrical stimulation of the nerve.

Signal receiver 12/12' receives, detects, and records a response signal, which is generated by body BO in response to stimulations (e.g., from the brain). Signal receiver 12/12' receives the signal from one or more recording electrodes. In some embodiments, an implantable NMES device couples to stimulating and recording electrodes and performs the functions of both stimulator 11 and signal receiver 12. Preferably, the recording electrodes are configured to record an evoked potential generated by a nerve in the lumbar portion of the back, such as the medial branch of the dorsal ramus. As such, the recording electrodes are configured to be: implanted within the patient on, around, or near a target nerve in the lumbar portion of the back, or applied externally over or near the location of the target nerve. In other embodiments, signal receiver 12 is a separately implanted recording device.

In still other embodiments, signal receiver 12 is an external device, such as an external controller, which may include a processor programmed to receive and record signals received from external recording electrodes. External recording electrodes can be placed in a suitable place for receiving the response signals, e.g., in the vicinity of the stimulated nerves or muscles, or on the skull over the cortex of the brain.

Signal processor 13/13' processes the recorded signal, for example, by amplifying, filtering, digitizing and temporal averaging the recorded signal to form a processed signal. Signal processor 13/13' may additionally analyze the processed signal to identify clinically meaningful data, such as, for example, the average amplitude, peak amplitude, frequency, shape, or slope of the processed signal. Signal processor 13/13' receives the recorded signal from signal receiver 12/12'. Signal processor 13/13' of various embodiments is a computer processor configured, for example, with programmed instructions, to perform signal processing, and optionally, signal analysis functions. In some embodiments, the functions of signal processor 13/13' are performed by a plurality of computer processors located within separate apparatuses. For example, in some embodiments, amplification and filtering of the signal occurs within a first device and digitizing and temporal averaging of the signal occurs within a second device. Signal analysis may occur within a third device. Some or all signal processor 13/13' functions may be performed by an implantable NMES device or a separately implanted recording device. Additionally or alternatively, some or all signal processor 13/13' functions may be performed by an external device, such as an external controller or programming computer.

As depicted, system 10 of FIG. 1A also includes user input receiver 14, optional stimulation activator 15, trigger detector 16, and output display 17. Similarly, depicted system 10' of FIG. 1B also includes user input receiver 14', trigger detector 16', and output display 17'. Within stimulation monitoring system 10/10', user input receiver 14/14' functions to receive instructions from a user for selecting a stimulation protocol and adjusting stimulation parameters. For example, using user input receiver 14/14', a user may be able to program the strength, duration, pulse pattern, frequency, start time, and/or stop time of the stimulations. User input receiver 14/14' functionality may be performed by any suitable input device known to those skilled in the art, such as, for example, a mouse, a keyboard, one or more knobs, one or more buttons, or a touchscreen. User input receiver 14/14' is configured to transmit signals indicative of the user input via wired and/or wireless communication to stimulation activator 15, stimulator 11, and/or TMS control unit 19 using known communication techniques.

In the embodiment of FIG. 1A, optional stimulation activator 15 transmits the instructions received from a user from user input receiver 14 to stimulator 11 via wired or wireless communication using known communication techniques. The instructions are transmitted in the form of electrical signals. As an example, when stimulator 11 is an implantable NMES device, stimulator activator 15 is an external device having an external controller that is communicatively coupled to an input receiver 14. The external controller transmits signals received from input receiver 14 to the NMES device in order to start, stop, set, and/or modulate the stimulation signal in accordance with instructions received from the user. As described in more detail below, the external controller may include an inductive coil or other antenna operable to wirelessly transmit the signals across the skin to the internally-positioned NMES device.

In other embodiments, when the stimulating means is an external stimulating device such as a TMS system (including TMS control unit 19 and coil 18), stimulator activator 15 may not be required. In such embodiments, stimulation parameters and instructions to start and stop stimulation may be communicated directly from input receiver 14' to the TMS control unit 19. In one embodiment, user input receiver 14' is integrated into TMS control unit 19 such that TMS control unit 19 also performs the functions of user input receiver 14' and no separate device or external transmission of signals is required.

Trigger detector 16 communicates with stimulator 11 and identifies when a stimulus has been generated. Similarly, trigger detector 16' communicates with TMS control unit 19 to identify when a stimulus has been generated. Trigger detector 16/16' also communicates with signal processor 13/13', sending data to signal processor 13/13' upon identifying a stimulus. Data received from trigger detector 16/16' initiates signal processing and analysis by signal processor 13/13' and thereby enables synchronization of the response signal with the stimulus. Advantageously, synchronization of the response signal with the stimulus enables accurate temporal averaging. Trigger detector 16 functionality may be performed by an external controller that is coupled to an external signal processing device and an implanted stimulating device. Alternatively, trigger detector 16/16' functionality may be performed by an external controller that is coupled to an external stimulating device and an implanted signal processing device.

Output display 17/17' provides feedback and stimulation results to a user. For example, output display 17/17' may display a graphical user interface (GUI) that provides a user with a visual representation of the stimulation signal and/or the processed signal. Additionally or alternatively, output display 17/17' may display a GUI that provides a user with visually presented numeric data indicative of the recorded response signal or the processed signal. Such data may include the average amplitude, peak amplitude, frequency, or slope of the processed signal or other data calculated by the signal processor. The output display may include a touchscreen, or other screen, display, or other output device for presenting or communicating results. In some embodiments, output display 17/17' and user input receiver 14/14' are integrated into a common device such as a laptop, tablet, smart phone, or other computing device.

From the visual representations displayed in the GUI of output display 17/17', a healthcare provider may be able to identify one or more characteristics and/or reach one or more diagnoses or other conclusions regarding the muscle(s) targeted for stimulation. For example, a healthcare provider may be able to identify quantitative metrics characteristic of recently denervated and innervated muscle from information displayed within the GUI. Recently denervated muscle may be identified, for example, by sharp positive waves and/or fibrillation; recently innervated muscle may be identified, for example, by polyphasic potentials. One or more systems and/or methods provided herein may enable tracking of re-innervation.

Figure 2A:
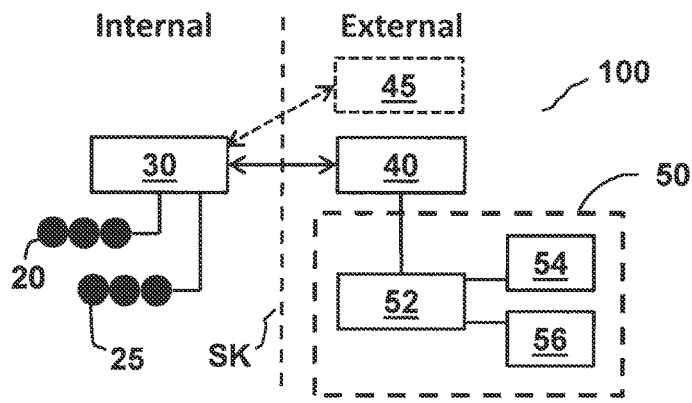

Referring to FIG. 2A, a block diagram of the structural components in one embodiment of a stimulation monitoring system is provided. In system 100, various components of system 100 are implanted while other components are extracorporeal. In particular, in FIG. 2A, NMES device 30 is implanted within the body and is configured to perform functions similar to those described above with respect to stimulator 11 of FIG. 1A. In the depicted embodiment, NMES device 30 is also configured to perform functions similar to that of signal receiver 12 and at least some of the functions performed by signal processor 13 in FIG. 1A. Computer 50 may optionally perform additional functions performed by signal processor 13. Computer 50 is further configured to perform the functions of user input receiver 14 and output display 17. Stimulation activator 15 functions may be performed by external controller 40. If the signal processing steps of signal synchronization and temporal averaging are performed by computer 50, then external controller 40 also performs functions similar to trigger detector 16. Alternatively, NMES device 30 may perform such signal processing steps and the functions of trigger detector 16.

In FIG. 2A, NMES device 30 is a pulse generator connected to a plurality of stimulating electrodes 20, e.g., via one or more leads having the electrodes disposed thereon, for delivering one or more electrical pulses to a portion of body BO. Stimulating electrodes 20 may be situated close to or around a peripheral nerve such as at or close to where the nerve enters skeletal muscle. In a preferred embodiment, stimulating electrodes 20 may be situated on or near the medial branch of the dorsal ramus nerve, which innervates the lumbar multifidus. Stimulating electrodes 20 may deliver neuromuscular electrical stimulation pulses to the nerve.

In this and other embodiments described herein, the various stimulating means (e.g., stimulating electrodes and pulse generators or TMS control units and coils) may induce contraction of the muscle to achieve, over time, restoration of neural control and rehabilitation of the muscle, as described in the aforementioned U.S. Pat. Nos. 8,428,728 and 8,606,358 to Sachs. Additionally or alternatively, stimulating means can be configured to deliver electrical stimulation of a sufficiently low strength that it does not elicit muscle contractions, but may stimulate the proprioceptive (i.e.: afferent) pathways, thereby providing input to the brain to help restore neural control and rehabilitation of the muscle. Appropriate selection of stimulation parameters may cause both muscle contraction and proprioceptive signals.

NMES device 30 also may be connected to recording electrodes 25 to receive signals, including evoked potentials, recorded from the body BO. In the depicted embodiment, implanted stimulating electrodes 20 and recording electrodes 25 are separate electrodes disposed on separate leads; however, it will be appreciated by one skilled in the art that one set of electrodes positioned on one lead may function as both stimulating and recording electrodes. Alternatively, a set of stimulating electrodes and a separate set of recording electrodes may be positioned on the same lead. Recording electrodes 25, if disposed on a lead separate from the stimulating electrode lead, may be implanted near to or remote from the stimulating electrodes. As would be apparent to one of ordinary skill in the art, various electrode locations and configurations would be acceptable, including the use of one, two, three, four, or more electrodes. The electrode(s) may be an array of a plurality of electrodes, or may be a simple single electrode where the electrical circuit is completed with an electrode placed elsewhere (not shown) such as a skin surface patch.

NMES device 30 may be controlled by, and optionally powered by, external controller 40, which communicates with NMES device 30 via an antenna, which may comprise an inductive coil configured to transmit power and communicate information in a bidirectional manner across skin SK. Appropriate antenna technology is well known to one skilled in the art and may include a magnet, a coil of wire, a longer range telemetry system (such as using MICS RF Telemetry available from Zarlink Semiconductor of Ottawa, Canada), or technology similar to a pacemaker programmer. Alternatively, a coil may be present within external controller 40 to transmit power only, and/or separate radio frequency transmitters may be provided in external controller 40 and NMES device 30 for establishing bi-directional data communication.

External controller 40 may be hardwired, connected by a cable, or wirelessly connected, to computer 50. Computer 50 may be a conventional laptop, desktop, or tablet computer having a microprocessor 52, an input device 54, and an output device 56. In certain embodiments, the input device 54 includes a mouse and a keyboard and the output device 56 includes a display screen. In other embodiments, a touchscreen forms both the input device 54 and the output device 56.

In the illustrated embodiment, software may be installed in memory and executed by processor 52 within computer 50, and used by a clinician to provide programming that is communicated by external controller 40 to NMES device 30. During patient visits, external controller 40 may be coupled to computer 50 to download for review data stored on NMES device 30, or to adjust the operational parameters of the NMES device.

In use, computer processor 52 runs a software application, which enables a clinician to select a stimulation protocol and/or adjust stimulation parameters by entering selections using input device 54. These inputs are delivered by computer 50 to external controller 40, which wirelessly conveys such inputs to NMES device 30. NMES device 30 generates a stimulation protocol in accordance with the inputs, delivering one or more electrical pulses to a portion of a patient's body BO via stimulating electrodes 20. Such stimulation elicits an electrical signal, namely, an evoked potential, from the nervous system NS of the body BO in response. There are also other signals present within the body BO. These signals can create noise for stimulation monitoring system 100. Thus, when recording electrodes 25 record a signal from body BO, it may contain both noise and the evoked potential. The recording electrodes 25 deliver the signal containing the evoked potential to NMES device 30 via a lead. NMES device 30 stores, amplifies, and digitizes the signal for wireless transmission to external controller 40, which in turn communicates it to computer 50.

While external controller 40 is generally described herein as being a single device, one skilled in the art will appreciate that the functions of external controller 40 may be performed by two or more devices. For example, as shown in FIG. 2A, the system may include external controller 40 and optional remote controller 45. In such embodiments, external controller 40 is coupled to computer 50 and configured to receive programming data, such as stimulation protocol data, from computer 50. External controller 40 further is configured to transmit the data to NMES device 30 to program NMES device 30 for operation. Remote controller 45 may include an interface, processor, and communication means and be configured to transmit signals to NMES device 30 to start and stop individual stimulation sessions. Such a system is described in more detail in U.S. Application Publication No. 2014/0046308 to Sachs et al., which is incorporated herein by reference in its entirety. While not shown, it is herein contemplated that external controller 40' of FIG. 2B and external controller 40" of FIG. 2C may also be embodied in two or more separate devices, such as an external controller and a remote controller.

Further processing of the signal may be performed to improve the signal-to-noise ratio of the evoked potential in order to increase the accuracy of stimulation monitoring. In the depicted embodiment, such processing may be performed by NMES device 30 and/or programming computer 50. The signal processing may include: amplification, for example, by an operational amplifier; filtering, for example, by a low-pass, high-pass, and/or band-pass filter; digitizing; and averaging, for example, by temporal averaging. Such processing of the recorded response signal creates a processed signal, which may be analyzed to identify and provide measurements of interest to the clinician. Such analysis also may be performed by NMES device 30 or computer processor 52. Data indicative of the processed evoked potential signal may then be displayed to the clinician on output device 56.

Figure 2B:
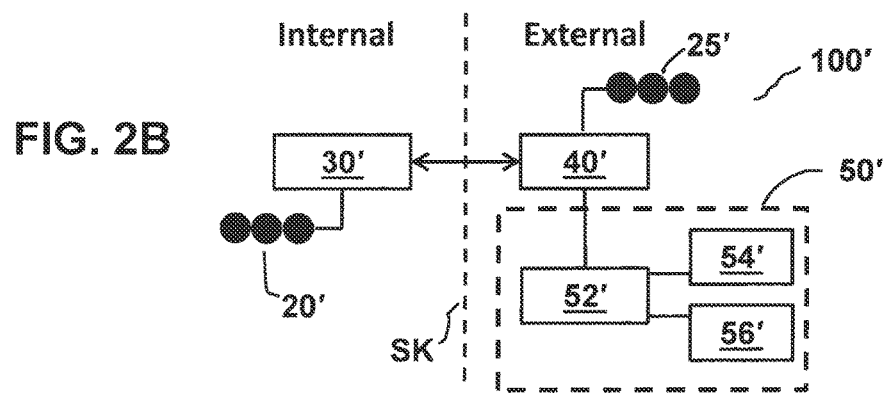

Referring to FIG. 2B, stimulation feedback system 100' is constructed similarly to feedback system 100 of FIG. 2A, wherein like components are identified by like-primed reference numbers. Thus, for example, 30' in FIG. 2B corresponds to 30 of FIG. 2A, etc. As will be observed by comparing FIGS. 2A and 2B, NMES device 30' is not directly connected to recording electrodes 25'; it is configured to stimulate only. NMES device 30' is connected to stimulating electrodes 20' to deliver one or more electrical pulses to a portion of patient's body BO. Similar to FIG. 2A, a clinician can interact with computer 50' having microprocessor 52', input device 54', and output device 56' to input new stimulation parameters, adjust existing parameters, and receive visual feedback in the form of data about evoked potentials to monitor the effects of stimulation. In FIG. 2B, computer 50' is hardwired, connected by a cable, or wirelessly connected to external controller 40', which in turn, is wirelessly coupled to NMES device 30'. In the depicted embodiment, external controller 40' is also coupled to externally located recording electrodes 25'. Such recording electrodes 25' may be disposable or reusable skin surface electrodes, needle electrodes, or fine wire electrodes. External recording electrodes 25' are applied over a suitable location to detect evoked potentials. The recording electrodes may be placed on the patient over the spinal column, on the scalp, or over the muscle of interest; in some embodiments, recording electrodes 25' are placed over or near the lumbar multifidus muscle. In some embodiments, a plurality of recording electrodes are placed so as to record signals from a plurality of locations on the patient's body.

In the depicted embodiment, NMES device 30' performs stimulator 11 functions, while a microprocessor unit within external controller 40' performs stimulation activator 15, trigger detector 16, and optionally, signal processor 13 functions. External controller 40' also performs signal receiver 12 functions. Computer 50' may additionally or alternatively perform signal processing 13 functions. Computer 50' additionally performs user input receiver 14 and output display 17 functions.

As will be appreciated by one of ordinary skill in the art, while NMES device 30 and 30' are illustratively implantable, these devices may be disposed external to a body of a patient on a temporary or permanent basis without departing from the scope of the present invention. In such an embodiment, NMES device 30 or 30' may be coupled to electrodes by percutaneous leads. Alternatively, the NMES device and the electrodes may be completely external such that the leads are applied to the skin over a suitable location to elicit muscle stimulation and contraction.

Figure 2C:
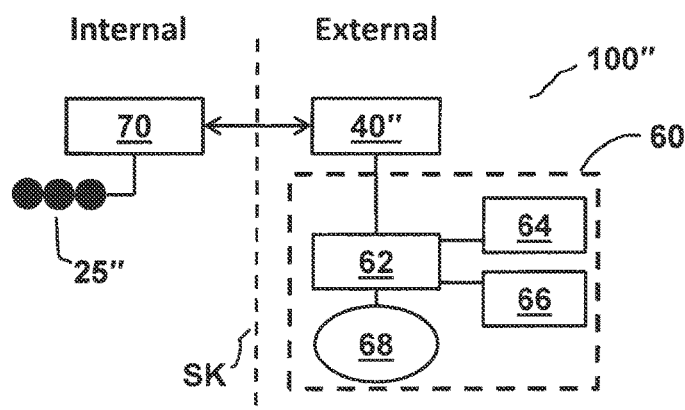

Referring to FIG. 2C, stimulation feedback system 100" is constructed to perform similar functions as feedback system 100 of FIG. 2A. In FIG. 2C, components analogous to components of FIG. 2A are identified by analogous-double primed reference numbers. As will be observed by comparing FIGS. 2A and 2C, no NMES device or stimulating electrode is present in stimulation monitoring system 100". Rather, stimulations are generated by TMS system 60 and applied to body BO externally via electromagnetic coil 68. As in FIG. 2A, the stimulations can be directed to cause stimulation and contraction of a muscle, such as a muscle of the local muscle system of the back. Preferably, the stimulations may be directed to cause stimulation and contraction of the lumbar multifidus or other lower back muscle to rehabilitate said muscle.

In use, processor 62 of TMS system 60 runs a software application, which enables a clinician to set and/or adjust stimulation parameters by entering such parameters using input device 64. TMS system 60 generates a stimulation protocol in accordance with the parameters, applying an electromagnetic field over a portion of the patient's brain, such as the motor cortex or a portion thereof, in order to deliver a stimulating electric current to the patient. Such stimulation elicits an electrical signal, namely, an evoked potential, from the nervous system NS of the body BO in response. Implanted recording electrodes 25" record a signal from the body BO, which may contain the evoked potential, and additionally, noise. Recording electrodes 25" then deliver the signal to implanted recording device 70 to which the recording electrodes are coupled via a lead. Implanted recording device 70 stores, amplifies, and digitizes the signal so the digitized signal (or a more processed version thereof) can be wirelessly communicated to external controller 40". In turn, external controller 40" communicates the digitized signal (or a processed version thereof) back to TMS system 60.

As in FIG. 2A, the signal is processed to improve the signal-to-noise ratio of the recorded response signal (e.g., the evoked potential) in order to increase the accuracy of stimulation monitoring. Signal processing may include amplification, filtering, digitizing, and temporal averaging. Such processing creates a processed evoked potential signal, which may be analyzed to identify and provide measurements of interest to the clinician. Signal processing and analysis may be performed by one or more of: implanted recording device 70, external controller 40", and TMS system 60. Data indicative of the processed evoked potential signal may be displayed to the clinician on output device 66. Output device 66 of some embodiments is a display screen provided within TMS system 60.

In the depicted embodiment, components of TMS system 60 perform user input receiver 14', TMS control unit 19, coil 18, and output display 17 functions. Implanted recording device 70 performs signal receiver 12', and optionally, signal processing 13' functions. External controller 40" and/or TMS system 60 may additionally or alternatively perform signal processing 13' and trigger detector 16' functions.

Figure 3A:
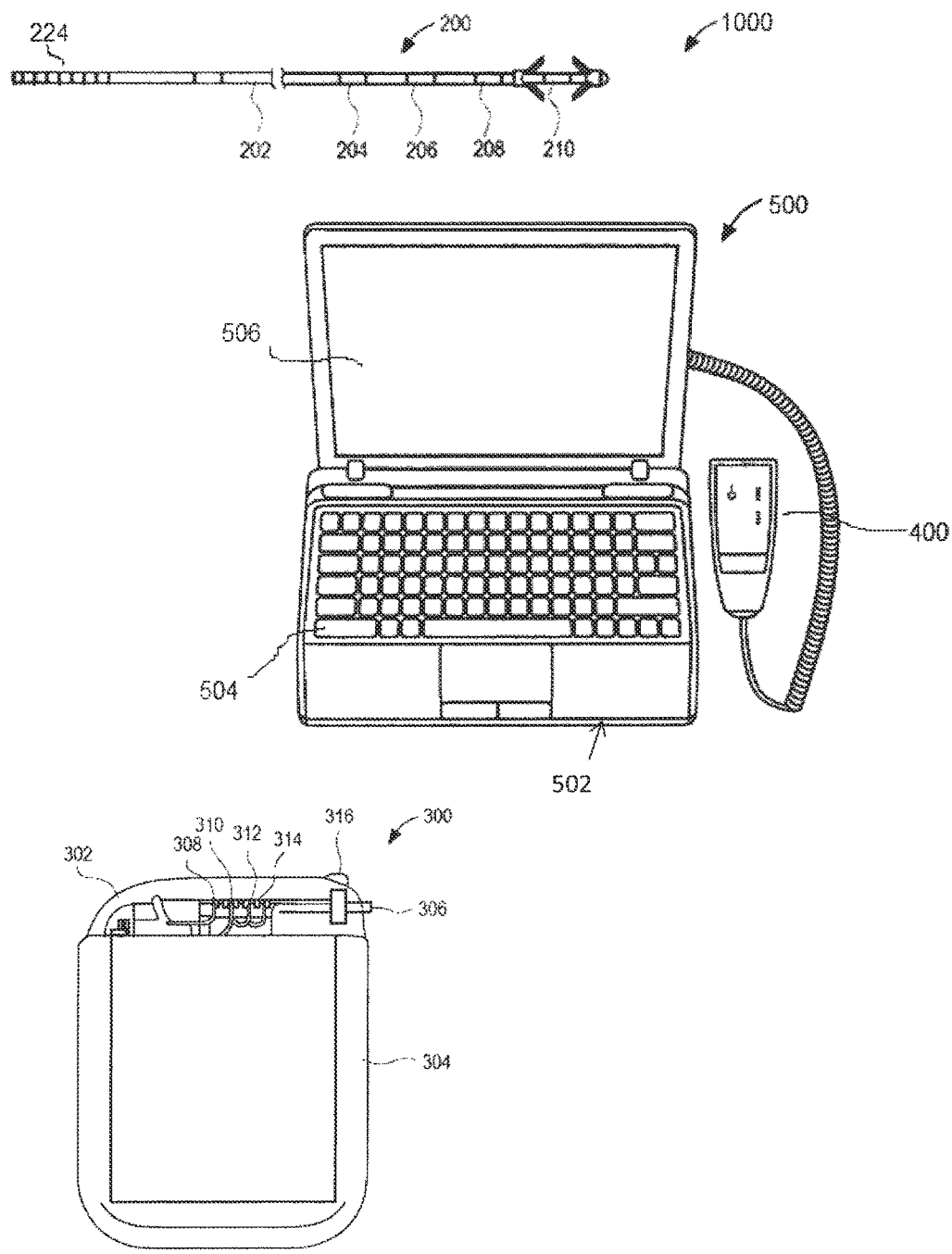
FIG. 3A depicts a schematic view of some or all components forming an exemplary embodiment of a stimulation monitoring system constructed in accordance with the principles of the present invention. In the depicted system, an implantable NMES device generates stimulation pulses and further records response signals.

Referring now to FIG. 3A, one exemplary embodiment of stimulation monitoring system 1000 is described. Specifically, FIG. 3A provides a generalized schematic view of components similar to those depicted as blocks in FIG. 2A. In FIG. 3A, components of the system are not depicted to scale on either a relative or absolute basis. Stimulator system 1000 includes electrode lead 200, NMES device 300 in the form of implantable pulse generator (IPG), external controller 400, and programming computer 500.

Electrode lead 200 includes lead body 202 having a plurality of electrodes, illustratively, electrodes 204, 206, 208, and 210. Electrode lead 200 is configured for implantation in or adjacent to tissue, e.g., nervous tissue, muscle, a ligament, and/or a joint capsule including tissue associated with local segmental control of the lumbar spine. Electrode lead 200 is coupled to NMES device 300, for example, via connector block 302. NMES device 300 is configured to generate pulses such that electrodes 204, 206, 208, and/or 210 deliver neuromuscular electrical stimulation to target tissue. In one embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain. Additionally or alternatively, such stimulation may stimulate the proprioceptive pathways, thereby providing input to the brain to help restore neural control and rehabilitation of the muscle. The electrodes may be ring electrodes, partial electrodes, segmented electrodes, nerve cuff electrodes placed around the nerve innervating the target muscle, or the like. Additionally, as will also be understood by one of skill in the art, an electrode lead may contain more or fewer than four electrodes.

In some embodiments, electrodes 204, 206, 208, and 210 of electrode lead 200 both deliver and record electrical signals. In other embodiments, one or a plurality of electrodes on electrode lead 200 stimulate while one or a plurality of different electrodes on electrode lead 200 record. In still other embodiments, system 1000 includes at least two leads, a first lead with a set of stimulating electrodes and a second lead with a set of recording electrodes.

NMES device 300 is configured to generate pulses for electrical transmission to electrode lead 200. As is common with other active implantable medical devices, the NMES device electronics are housed in a hermetically sealed metal housing 304. Housing 304 may comprise titanium or other biocompatible material, and includes connector block 302 that permits electrode lead 200 to be electrically coupled to the electronics within housing 304 via channel 306. Channel 306 is coupled to conductors 308, 310, 312, and 314 which are coupled to the NMES device electronics. When proximal end 224 of electrode lead 200 is inserted within channel 306, conductors 308, 310, 312, and 314 are electrically coupled to a plurality of contacts on the proximal end 224, which are, in turn, electrically coupled to electrodes 204, 206, 208, and 210. Set-screw 316 is configured to be tightened down on set-screw retainer 244 to secure a portion of electrode lead 200 within channel 306. NMES device 300 further may include a second channel (not shown) with four additional conductors. The two separate channels may be used to facilitate bilateral stimulation or may be used to attach separate leads for stimulating and recording.

External controller 400 is configured to control the internal functional components of NMES device 300 by transmitting instructions from external programming computer 500 to the NMES device. In the depicted embodiment, external controller 400 is further configured to receive digitized signals containing evoked potentials from NMES device 300 and deliver them to external programming computer 500 for further processing, analysis, and/or display of the stimulation results. External controller 400 includes a telemetry component that permits transmission of energy and data between NMES device 300 and programming computer 500. The telemetry component may comprise an inductive coil or RF transceiver configured to communicate information in a bidirectional manner across a patient's skin SK to NMES device 300, and optionally, to transmit power to NMES device 300.

Optionally, external controller 400 may include a commercially available microcontroller unit including a programmable microprocessor and memory for processing signals received from NMES device 300. In the depicted embodiment, external controller 400 functions primarily as a signal intermediary between implanted NMES device 300 and extracorporeal programming computer 500, and all signal processing and analysis is performed by the NMES device and/or the programming computer.

Programming computer 500 includes a programmable microprocessor, nonvolatile memory such as EEPROM, and nonvolatile storage, e.g., Flash memory. The memory of programming computer 500 may store program instructions that, when executed by processor 502 of programming computer 500, cause the processor and NMES device 300 to provide the functionality ascribed to them herein.

Figure 3B:
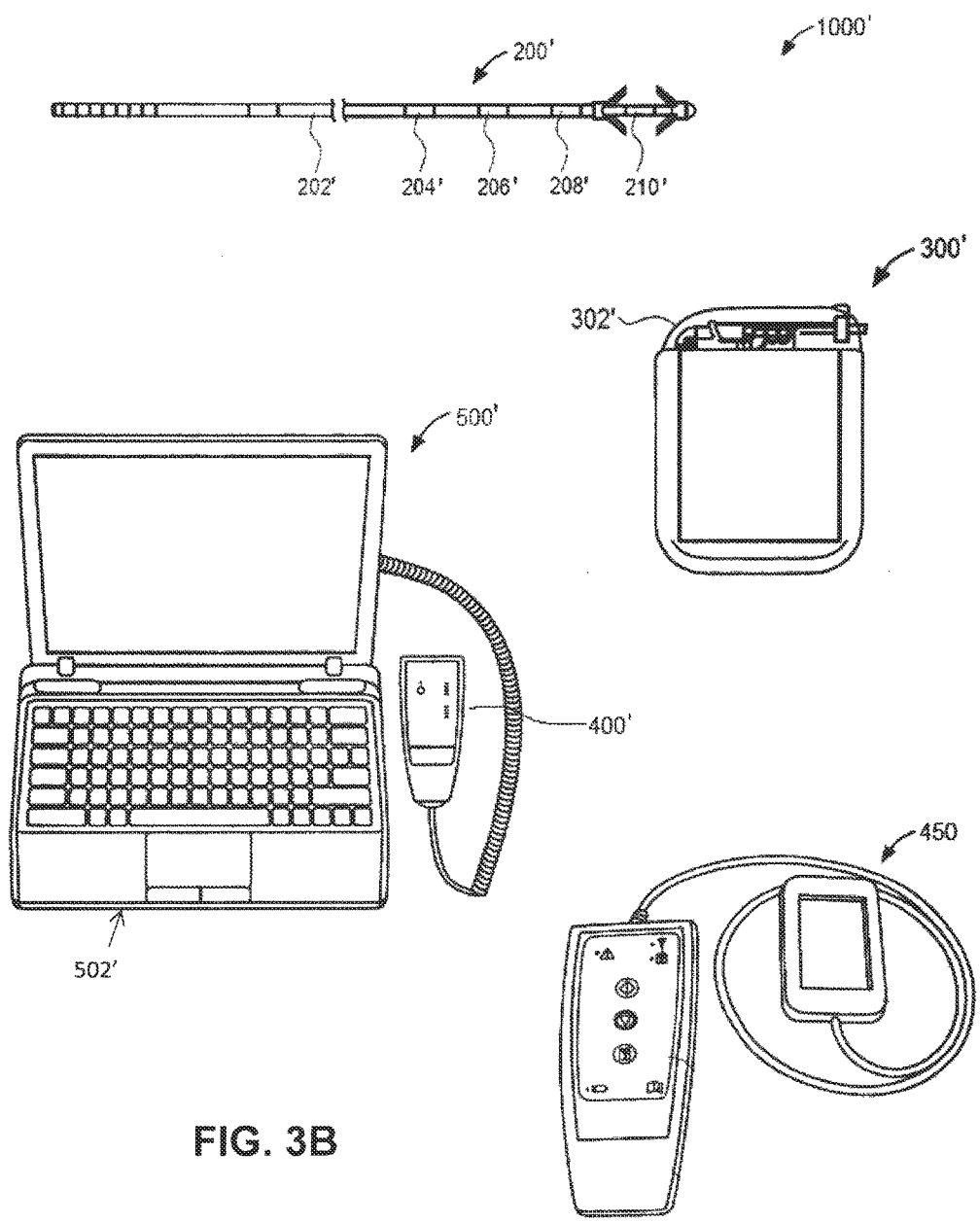
FIGS. 3B and 3C depict alternative schematic views of the stimulation monitoring system of FIG. 3A, wherein the system of FIG. 3B has an implantable NMES device similar to FIG. 3A with additional external components provided, and the system of FIG. 3C has an externally located TMS device for generating stimulations and an implantable recording device for recording response signals.

Referring to FIG. 3B, stimulation feedback system 1000' is constructed similarly to feedback system 1000 of FIG. 3A, wherein like components are identified by like-primed reference numbers. Thus, for example, 300' in FIG. 3B corresponds to 300 of FIG. 3A, etc. As will be observed by comparing FIGS. 3A and 3B, in FIG. 3B, the system 1000' includes an additional component. Specifically, FIG. 3B includes both external controller 400' and remote controller 450. Together, these components perform the functions performed by external controller 400 in FIG. 3A. For example, external controller 400' may be used within a clinician's office to program implanted NMES device 300' and remote controller 450 may be used by a user such as a patient to control a limited number of operational parameters, including starting and/or stopping individual stimulation sessions. Both external controller 400' and remote controller 450 may be configured to transmit signals wirelessly to NMES device 300' using known wireless communication techniques. Such a system set up is described in more detail in U.S. Application Publication No. 2014/0046398 to Sachs et al., which is incorporated herein by reference in its entirety.

Figure 3C:
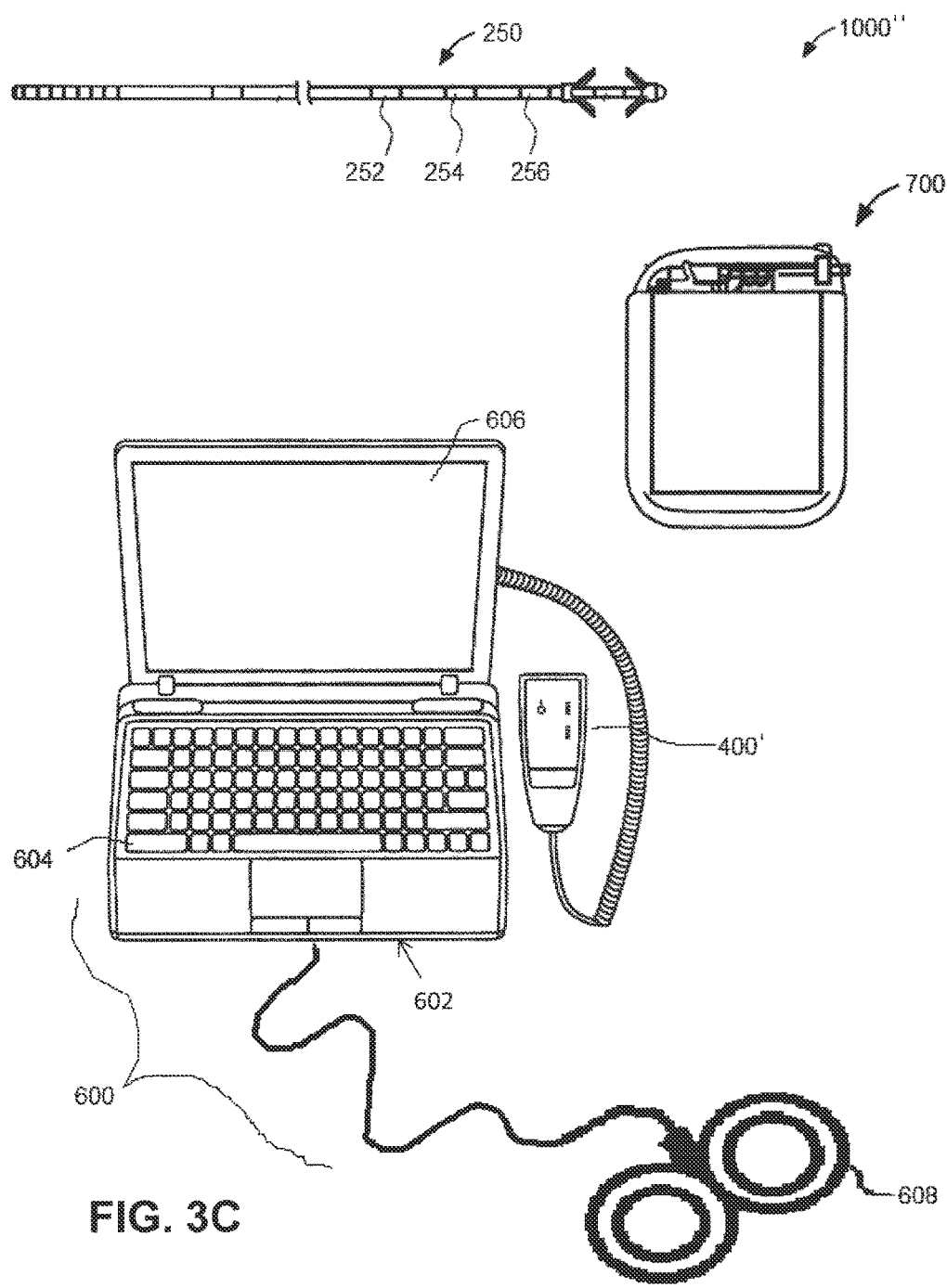

Referring to FIG. 3C, stimulation feedback system 1000" is constructed to perform similar functions as feedback system 1000 of FIG. 3A. In FIG. 3C, components analogous to components of FIG. 3A are identified by analogous-double primed reference numbers. As will be observed by comparing FIGS. 3A and 3C, no NMES device or stimulating electrode is present in stimulation monitoring system 1000". Rather, stimulations are generated by TMS system 600 and applied to a patient externally via electromagnetic coil 608.

TMS system 600 is formed of a plurality of components including input device 604, output device 606, processor 602, and electromagnetic coil 608. In the depicted embodiment, input device 604, output device 606, and processor 602 together form portions of a computing device having the same or similar properties as computer 500 of FIG. 3A. Such a computing device may be a tablet computer, a laptop computer, a desktop computer, or mobile computing device. Electromagnetic coil 608 is shown connected to the computing device and may be controlled via a wired or wireless connection. In another embodiment, the various components of TMS system 600 form a specialized and integrated TMS device. The computer within the specialized TMS device may still have the same or similar properties as computer 500 of FIG. 3A.

In FIG. 3C, input device 604 is configured to receive inputs from a user, such as a clinician, to set and/or adjust stimulation parameters for system 1000". Processor 602 is configured to process user inputs received at input device 604 and activate electromagnetic coil 608 based on the user inputs. In use, stimulations in accordance with the user-set stimulation parameters are applied via electromagnetic coil 608, which is positioned and configured to apply an electromagnetic field over a portion of a patient's brain, such as the motor cortex. The electromagnetic field generates a stimulating electric current. Such stimulation elicits an electrical signal, namely, an evoked potential, from the nervous system. Preferably, electrode lead 250 is implanted on, around, adjacent, or near a nerve of interest, such as a nerve of the lumbar back region, such that, when an evoked potential is generated by the nerve, one or more recording electrodes 252, 254, or 256 on electrode lead 250 record the signal. In use, recording electrode lead 250 is connected to an implanted recording device 700 and configured to transmit recorded signals to recording device 700 for storage, amplification, and digitization. Recording device 700 may contain software and/or hardware to enable such signal processing steps. Recording device 700 is further configured to wirelessly communicate the digitized signal to external controller 400" via known wireless communication technology. In turn, external controller 400" is configured to send the digitized signal to TMS system 600. External controller 400" may be connected to at least a portion of TMS system 600 via a wired or wireless connection. TMS system 600 may perform additional processing of the digitized signal, and output device 606 is configured to display, for example, via a GUI, data indicative of the evoked potential found within the digitized signal.

Figure 4:
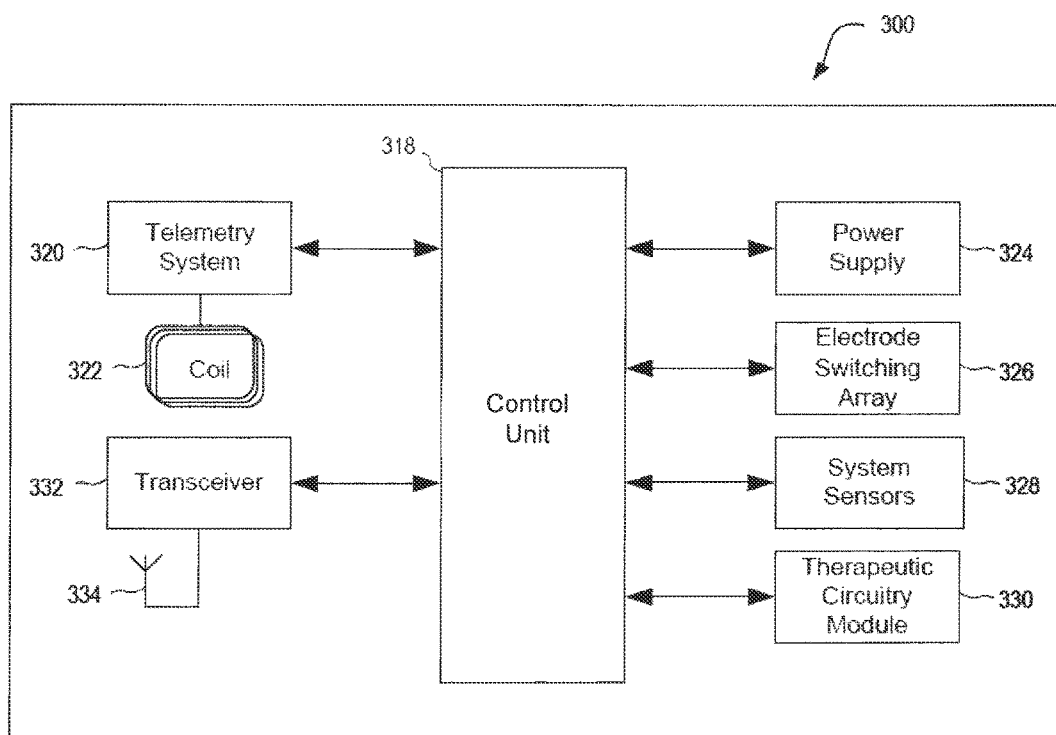
FIG. 4 depicts a generalized block diagram of an implantable NMES device, such as the NMES device of FIG. 3.

The internal functional components of an NMES device are represented in a generalized schematic diagram in FIG. 4. While the following description makes reference to NMES device 300 of FIG. 3A, this is done for ease of reference only, and those skilled in the art will understand that some of or all the features described herein with respect to NMES device 300 may be present in NMES device 300' and/or in implanted recording device 700.

NMES device 300 may include control unit 318, means of bidirectional communication with external controller 400, power supply 324, electrode switching array 326, system sensors 328, and optional therapeutic circuitry module 330. The means of bidirectional communication may comprise one or both of telemetry system 320 coupled to coil 322 and a communications circuit employing transceiver 332 coupled to antenna 334.

Control unit 318 is electrically coupled to, and configured to control, the internal functional components of NMES device 300. Control unit 318 may comprise a commercially available microcontroller unit including a programmable microprocessor, volatile memory, nonvolatile memory such as EEPROM for storing programming, and nonvolatile storage, e.g., Flash memory, for storing a log of system operational parameters and patient data. The memory of control unit 318 may collect and store all signals containing evoked potentials (raw or processed) that are received from recording electrodes during therapeutic stimulations until such signals can be transmitted to a clinician's programming computer. The memory of control unit 318 further stores program instructions that, when executed by the processor of control unit 318, cause the processor and the functional components of NMES device 300 to provide the functionality ascribed to them herein. Control unit 318 is configured to be programmable such that programming data is stored in the memory of control unit 318 and may be adjusted using external controller 400 and programming computer 500. Programming data may include pulse amplitude (voltage or current), pulse width, stimulation rate, stimulation frequency, ramp timing, cycle timing, session timing, duty cycle, electrode configuration, location and number of contacts activated, and percent of total current allocated to each contact. In accordance with one embodiment, programmable parameters, their ranges, and nominal values are:

| Parameter | Min | Max | Nominal |
|---|---|---|---|
| Amplitude | 0 mA | 7.0 mA | 1 mA |
| Pulse Width | 25 µs | 500 µs | 200 µs |
| Rate | 1 Hz | 40 Hz | 20 Hz |
| On Ramp | 0 s | 5 s | 2 s |
| Off Ramp | | | |
| Cycle-On | 2 s | 20 s | 10 s |
| Cycle-Off | 20 s | 120 s | 20 s |
| Session | 1 min | 60 min | 30 min |

Control unit 318 may be programmable to allow electrical stimulation between any chosen combination of electrodes on the lead, thus providing a simple bipolar configuration. In addition, control unit 318 may be programmed to deliver stimulation pulses in a guarded bipolar configuration (more than 1 anode surrounding a central cathode) or NMES device housing 304 may be programmed as the anode, enabling unipolar stimulation from any of the electrodes.

Control unit 318 further may be programmed with a software program to calculate the impedance at electrode lead 200. For example, control unit 318 may direct power supply 324 to send an electrical signal to one or more electrodes which emit electrical power. One or more other electrodes receive the emitted electrical power and send a received signal to control unit 318 that runs the routine to calculate impedance based on the sent signal and the received signal.

Control unit 318 is optionally coupled to communications circuitry including telemetry system 320, which is electrically coupled to coil 322, that permits transmission of stimulation commands, and optionally power, between NMES device 300 and external controller 400 such that NMES device 300 may be powered, programmed, and/or controlled by programming computer 500 via external controller 400. For example, control unit 318 may start or stop a treatment session responsive to stimulation commands received from a corresponding telemetry system and coil of external controller 400 via coil 322 and telemetry system 320. As another example, control unit 318 may direct changes to at least one of pulse amplitude (voltage or current), pulse width, stimulation rate, stimulation frequency, ramp timing, cycle timing, session timing, duty cycle, electrode configuration, location and number of contacts activated, and percent of total current allocated to each contact, responsive to programming data received from external controller 400 via coil 322 and telemetry system 320.

The technology for telemetry system 320 and coil 322 is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer.

Alternatively, coil 322 may be used to transmit power only, and separate radio frequency (RF) transceiver 332 and antenna 334 may be provided in NMES device 300 and complementary RF transmitters may be provided in external controller 400 for establishing bidirectional or unidirectional data communication.

In another alternate embodiment, a communication circuit having transceiver 332 and antenna 334 may replace telemetry system 320 coupled to coil 322. In such an embodiment, transceiver 332 preferably comprises an RF transceiver and is configured for bi-directional communications via antenna 334 with a similar transceiver circuit disposed in external controller 400. For example, transceiver 332 may receive stimulation commands and programming data from external controller 400. Control unit 318 may direct changes to at least one of pulse amplitude (voltage or current), pulse width, stimulation rate, stimulation frequency, ramp timing, cycle timing, session timing, duty cycle, electrode configuration, location and number of contacts activated, and percent of total current allocated to each contact, including commands to start or stop a treatment session, in response to programming data and/or stimulation commands received from a corresponding transceiver and antenna of external controller 400. Transceiver 332 also may include a low power mode of operation, such that it periodically awakens to listen for incoming messages and responds only to those messages including the unique device identifier assigned to that NMES device. In addition, transceiver 332 may employ an encryption routine to ensure that messages sent from, or received by, NMES device 300 cannot be intercepted or forged.

In addition to receiving programming data from external controller 400, the means of bidirectional communication (telemetry system 320 coupled to coil 322 and/or communication circuit with transceiver 332 coupled to antenna 334) is configured to transmit signals back to external controller 400. In particular, the communication means may be used to transmit a recorded response signal, a processed version of the signal, and/or data reflective of the processed evoked potential signal to external controller 400 for delivery to programming computer 500 for analysis and/or presentation.

Power supply 324 powers the electrical components of NMES device 300, and may comprise a primary cell or battery, a secondary (rechargeable) cell or battery, or a combination of both. Alternatively, power supply 324 may not include a cell or battery, but instead comprise a capacitor that stores energy transmitted through the skin via a Transcutaneous Energy Transmission System (TETs), e.g., by inductive coupling or via microwave energy or via ultrasound. In a preferred embodiment, power supply 324 comprises a lithium ion battery.

Control unit 318 further may be coupled to electrode switching array 326 so that any subset of electrodes of the electrode leads may be selectably coupled to therapeutic circuitry module 330, described in detail below. In this way, an appropriate electrode set may be chosen from the entire selection of electrodes implanted in the patient's body to achieve a desired therapeutic effect. Electrode switching array 326 preferably operates at high speed, thereby allowing successive stimulation pulses to be applied to different electrode combinations. Electrode switching array 326 also may enable NMES device 300 to both stimulate and record stimulations. When NMES device 300 is not generating stimulation pulses, it is listening for electrical signals from recording electrodes 250 at the lead. In embodiments where one set of electrodes both stimulate and record, electrode switching array 326 makes it possible to adequately depolarize the electrodes after delivery of a stimulation pulse so the electrodes are prepared to receive electrical signals without distortion. In one preferred embodiment, the electrode switching array 326 enables NMES device 300 to quickly transition between, or simultaneously perform, stimulating on one set of electrodes and listening on a different set of electrodes, thus allowing overlap of the stimulation with the acquisition of the response signal.

System sensors 328 may comprise one or more sensors that monitor operation of the systems of NMES device 300, and log data relating to system operation as well as system faults, which may be stored in a log for later readout using programming computer 500. In one embodiment, system sensors 328 include a magnetic sensor configured to sense a magnetic field and to transmit a signal to control unit 318 based on the sensed magnetic field such that the control unit starts or stops a treatment session. In another embodiment, system sensors 328 include one or more sensors configured to sense muscle contraction and to generate a sensor signal based on the muscle contraction. Control unit 318 is configured to receive the sensor signal from system sensors 328 and may be configured to adjust the stimulation parameters based on the sensor signal. In one embodiment, system sensors 328 sense an increase or decrease in muscle movement and control unit 318 increases or decreases the stimulation frequency to maintain smooth and continuous muscle contraction.

In one embodiment, sensors 328 may include an accelerometer that senses movement or acceleration of a muscle caused by muscle contraction. The accelerometer may be a 1-, 2- or 3-axis analog or digital accelerometer that determines (for example) whether the patient is active or asleep or senses overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. In an additional embodiment, the sensors provided may include a magnetometer to determine direction on the earth's surface. The accelerometer (and/or magnetometer) may be used to determine the orientation of NMES device 300, and by inference the orientation of the patient, at any time. For example, after implantation, external controller 400 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance. In other embodiments, system sensors 328 may include a pressure sensor, a movement sensor, and/or a strain gauge configured to sense muscle contraction and to generate a sensor signal based on the muscle contraction, and in a further embodiment, various combinations of at least one of an accelerometer, a magnetometer, a pressure sensor, a movement sensor, and/or a strain gauge are included.

Sensors 328 also may include, for example, a humidity sensor to measure moisture within housing 304, which may provide information relating to the state of the electronic components, or a temperature sensor, e.g., for measuring battery temperature during charging to ensure safe operation of the battery. Data from the system sensors may be logged by control unit 318 and stored in nonvolatile memory for later transmission to programming computer 500.

As will be appreciated by one of ordinary skill in the art, system sensors 328 may be placed in a variety of locations including within housing 302, within or adjacent to the tissue that is stimulated, and/or in proximity to the muscle to be contracted and connected via a separate lead to NMES device 300. In other embodiments, sensors 324 may be integrated into one or more of the leads used for stimulation or may be an independent sensor(s) operatively coupled to NMES device 300 using, for example, radio frequency (RF) signals for transmitting and receiving data.

Controller 318 also may be coupled to optional therapeutic circuitry module 330 that provides any of a number of complimentary therapeutic stimulation, analgesic stimulation (such as Peripheral Nerve Field stimulation or Spinal Cord Stimulation), feedback, or ablation treatment modalities. NMES device 300 illustratively includes one therapeutic circuitry module 330, although additional circuitry modules may be employed in a particular embodiment depending upon its intended application, as described in U.S. Patent Application Publication No. 2011/0224665 to Crosby, assigned to the assignee of the present invention, the entire contents of which is incorporated herein by reference. Therapeutic circuitry module 330 may be configured to provide different types of stimulation, either to induce muscle contractions, to provide afferent nerve stimulation to mask the perception pain, or to block pain signals in afferent nerve fibers; to monitor muscle contractions induced by stimulation and adjust the applied stimulation regime as needed to obtain a desired result; or to selectively and intermittently ablate nerve fibers to control pain and thereby facilitate muscle rehabilitation.

Figure 5:
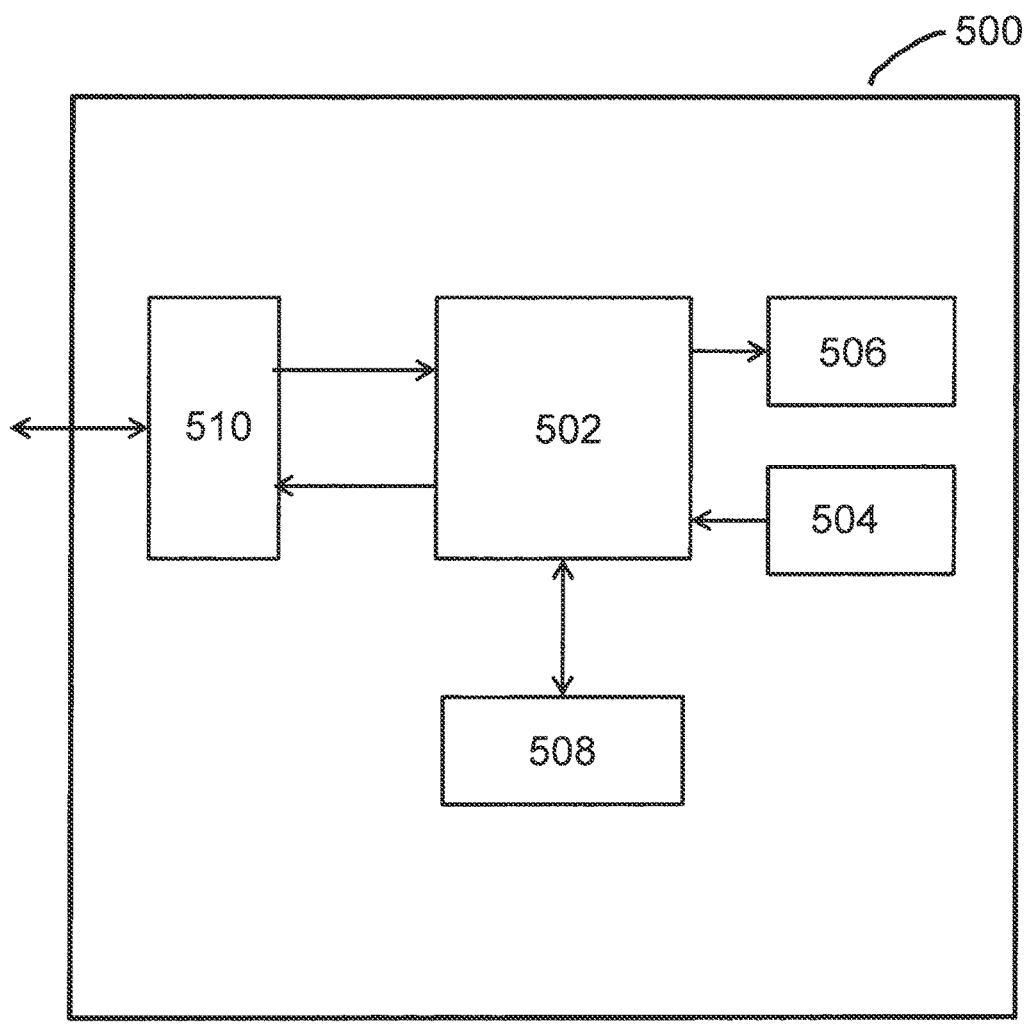
FIG. 5 depicts a generalized block diagram of a programming computer, such as the programming computer found in the system of FIG. 3.

FIG. 5 provides a functional block diagram of the internal components of programming computer 500. One skilled in the art will appreciate that the description of the components of programming computer 500 is also applicable to programming computer 500' and to TMS system 600 having processor 602 provided therein. Although described separately, it is to be appreciated that functional blocks need not be separate structural elements. For example, processor 502 and memory 508 may be embodied in a single chip; memory 508 may be embodied in volatile and non-volatile memory; and processor 502 and interface 510 may be embodied in a single chip.

Processor 502 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. Processor 502 also may be implemented as a combination of computing devices, e.g., a combination of a DSP and a microprocessor, a plurality of microprocessors, one or more microprocessors in conjunction with a DSP core, or any other such configuration.

Processor 502 is coupled, via one or more buses, to read information from and/or write information to memory 508. Processor 502 may additionally, or in the alternative, contain memory, such as processor registers. Memory 508 can include processor cache, including a multi-level hierarchical cache in which different levels have different capacities and access speeds. Memory 508 also may include random access memory (RAM), other volatile storage devices, or non-volatile storage devices such as hard drives, optical discs, flash memory, and solid state drives.

Processor 502, in conjunction with software stored in memory 508 executes an operating system, such as, for example, Windows, Mac OS, Mac iOS, Android, Unix, or Solaris. Processor 502 also executes software applications stored in memory 508. For example, memory 508 may store various stimulation protocols that provide any of a number of therapeutic stimulation, analgesic, feedback or ablation treatment modalities. Additionally or alternatively, memory 508 may store instructions for processing and analyzing recorded response signals received from NMES device 300 via external controller 400. Additionally or alternatively, memory 508 may store program instructions for a graphical user interface that enables a clinician to interact with programming computer 500 to provide appropriate user inputs needed to adjust one or more stimulation parameters, including pulse amplitude (voltage or current), pulse width, stimulation rate, stimulation frequency, and electrode configuration. In one non-limiting embodiment, the software comprises, for example, Unix Korn shell scripts. In other embodiments, the software can be written in any suitable programming language known to those skilled in the art, including, for example, C++, PHP, Ruby, or Java.

Processor 502 is also coupled to input device 504 and output device 506 for, respectively, receiving input from and providing output to, a clinician or other user. Suitable input devices include, but are not limited to, a keyboard, buttons, keys, switches, a pointing device, a mouse, a joystick, a remote control, a motion detector, and a microphone (possibly coupled to audio processing software to, e.g., detect voice commands). Suitable output devices include, but are not limited to, display screens, touchscreens, and audible output devices.

Processor 502 may be further coupled to input/output interface 510, which communicates signals generated by processor 502 to a coupled device, such as external controller 400, and similarly receives signals from the coupled device. In embodiments in which the coupled device is wirelessly coupled to processor 502, input/output interface 510 may include a wireless transceiver, which modulates and demodulates wirelessly communicated signals.

While exemplary components of stimulation monitoring system 100 have been depicted in FIGS. 2A-5 and described herein, it will be appreciated by one skilled in the art that exemplary, as used herein, means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure. The functional modules of stimulation monitoring system 100 depicted in FIG. 1 and the methods described below and elsewhere herein may be performed by the components described above, or, with the appropriate programmable instructions and electrodes, the functions and methods may be performed by the devices described in U.S. Appl. Pub. No. 2014/0058476 to Crosby or the devices described in U.S. Appl. Pub. No. 2014/0046398 to Sachs, each of which is incorporated herein by reference in its entirety.

Figure 6:
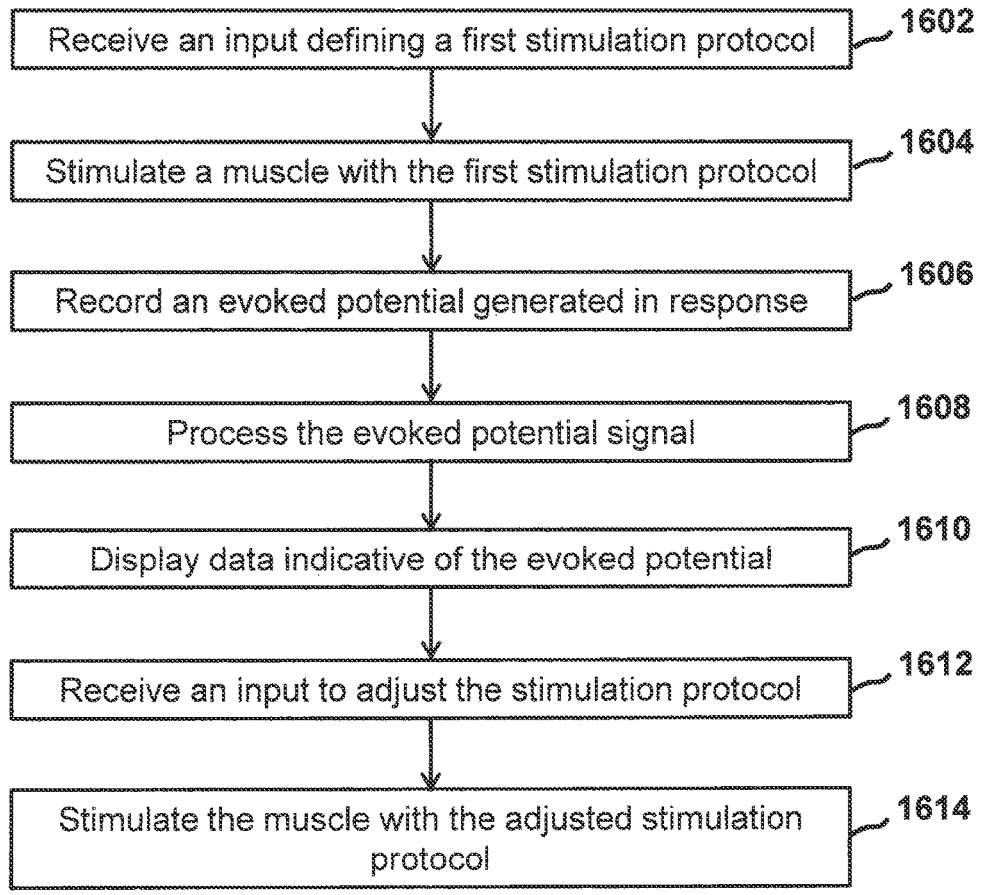
FIG. 6 depicts an exemplary method for applying, monitoring, and adjusting stimulation therapy in accordance with the principles of the present invention.

Referring now to FIG. 6, exemplary method 1600 for applying, monitoring, and adjusting stimulation therapy is provided. In a preferred embodiment, the method described herein is used to optimize the stimulation of skeletal muscles. The stimulation may be applied in order to cause contractions, and ultimately, to improve muscle strength and function. Additionally or alternatively, the stimulation may be applied to stimulate the proprioceptive pathways, and ultimately, to restore neural control and rehabilitate the muscle. For example, the method of one embodiment is used to optimize stimulation therapy to the lumbar multifidus or other back muscles in order to reactivate normal physiological control signals between the motor cortex and the back muscles to reduce dysfunction of the spinal stabilization system, stabilize the spine, and reduce lower back pain.

At step 1602 of method 1600, one or more inputs are received from a user, directly or indirectly, the inputs defining a first stimulation protocol that includes one or more electrical pulses. The inputs may be received by a device having a user interface coupled to a microprocessor, e.g., input device 54, 54', 64, 504, 504', or 604. The user may select the first stimulation protocol from a plurality of options presented in a graphical user interface; additionally or alternatively, the user may enter inputs for select individual parameters of the stimulation protocol. Such parameters may include one or more of: pulse amplitude (voltage or current), pulse width, stimulation rate, stimulation frequency, ramp timing, cycle timing, session timing duty cycle, electrode configuration, location and number of contacts activated, and percent of total current allocated to each contact. The user may be a clinician such as a surgeon or medical technician. The first stimulation protocol may provide for the application of therapeutic stimulations, such as stimulations intended to rehabilitate and strengthen a muscle and/or stimulations intended to stimulate the afferent nerve pathways and restore neural control. Alternatively, the protocol may provide for a diagnostic stimulation which merely stimulates a tissue of interest for purposes of observing and tracking the body's response to such stimulations. By tracking changes in the body's response over time, progress of a separately applied stimulation therapy or other therapy may be observable. Alternatively, the protocol may be provided for research purposes. By tracking changes in the body's response to changes in the location of motor cortex stimulation, mapping of the motor cortex, as it relates to control of various muscles, may be possible. In a preferred embodiment, the stimulation protocol is a therapeutic stimulation.

Any number of stimulation protocols may be available for selection or may otherwise be entered by the user. Exemplary protocols include application of: slow spaced pulses (e.g., 1-2 Hz), each of which results in a single muscle contraction; pulses that increase in frequency until a fusion frequency is reached (typically 12-15 Hz for type I/slow twitch muscles and 15-20 Hz for type II/fast twitch muscles); low intensity long duration pulses, which can inhibit nerve fiber depolarization; or "vibration" stimulation, which is comprised of electrical pulses having a greater frequency than pulses that elicit a single defined muscle contraction for each pulse but a lesser frequency than the fusion frequency, such a stimulation frequency (e.g., 2-10 Hz) may activate certain physiological structures or pathways responsive to vibration.

An exemplary stimulation protocol includes the following parameters: 10 seconds of stimulation at a frequency of 20 Hz, followed by 20 seconds of rest (no stimulation), repeated for 20 minutes. Such a protocol may be applied once, twice, or more per day.

Alternative stimulation regimes may be used for the first stimulation protocol and may be selected based on the particular situation of the patient being treated. For example, if the fundamental physiological problem is disruption to the afferent pathways (i.e., proprioceptive signals from the body to the brain), then a stimulation regime to maximize the afferent stimulation may result in better or more rapid outcomes. Such a stimulation regime could include short bursts of muscle contraction, such as, for example, 2 seconds of contraction followed by 2 seconds of relaxation, to generate more afferent stimulation at the onset and cessation of muscle contraction. In another example, if the fundamental physiological problem is inadequate strength of contraction of the lumbar multifidus muscle, then electrostimulation strength training of longer duration and higher force of contraction may result in better outcomes. Such a stimulation protocol may include, for example, 20 seconds of a frequency set at maximal contraction separated by 20 seconds of relaxation.

At step 1604, a muscle of a patient is stimulated with the first stimulation protocol, e.g., using electrode 20, 20', 200, or 200', or electromagnetic coil 68 or 608. The target muscle may be weak, injured, dysfunctional, or otherwise in need of rehabilitation. Stimulation may be generated by an NMES or TMS device, for example, and delivered by one or more stimulating electrodes.

At step 1606, a signal is recorded, e.g., using electrode 25, 25', 200, 200', or 250, the signal comprising an evoked potential generated by the patient's body in response to the first stimulation protocol. The signal may be picked up by one or more recording electrodes and recorded by an internally or externally placed signal receiving device. The signal may include a desired evoked potential and background noise. The signal may be recorded, for example, from EEG electrodes placed on the scalp, electrodes placed over the spine to record spinal reflex evoked potentials, fine wire or needle EMG electrodes placed in a muscle, dual stimulating/recording electrodes, or electrodes placed adjacent to or in a nerve at a location remote from the stimulating electrodes, including electrodes on or adjacent to a different nerve or electrodes on or adjacent to the same nerve at a different location.

The choice of stimulation determines the type of evoked potential elicited by the body. For example, in response to a single pulse repeated at a slow rate, the following evoked potentials may be detected: a rapid electrical response from the nerve to indicate nerve depolarization; several responses from the nerve spaced in time, including an evoked response from the spinal reflex arc; a rapid response from the muscle body indicating the degree of contraction; a later response, such as a spinal reflex or cortical response, from the muscle body indicating the control of the muscle in response to perturbation; and/or a response from the nerve indicating conduction of afferent signals such as from Golgi tendon organs, muscle spindles, or other mechanoreceptors. In response to stimulation at or above the fusion frequency, similar evoked potentials may be elicited and observed by properly placed recording electrodes. Additionally, when a fusion frequency stimulation is applied, the following additional event may be detected: change in EMG characteristics over time from the onset of contraction. Unique evoked potential responses also may be elicited by varying the stimulation between different intensities or by stimulating at the vibrating stimulation frequency.

At step 1608, the recorded signal is processed to produce a processed evoked potential signal, e.g., using NMES device 30, 30', 300, 300', implanted recording device 70, 700, and/or processor 52, 52', 62, 502, 502' or 602. Processing may include amplifying, filtering, digitizing, synchronizing, and/or temporal averaging the recorded signal. With temporal averaging, the electrical signals recorded following the stimulus are sampled using an analog-to-digital converter, then the time series of the samples is added together and divided by the number of samples to preserve scaling. The time series is synchronized with the stimulus event. For example, when a fusion frequency is applied, the evoked potential signal may be synchronized with the onset of the stimulation pulse train, the onset of force generation, a cessation of force generation, or a combination of the two. In this manner, the background signal, which is asynchronous to the stimulus, tends towards its mean of zero, and the evoked potential average tends to a useful value above the background noise. The signal-to-noise ratio improves with the square root of the number of responses that are averaged. The raw signal or the processed evoked potential signal may be stored in memory at least until a user is able to access the signal or information indicative of the signal via a user interface coupled to a computer.

At step 1610, data indicative of the evoked potential is displayed to the user. The data may be displayed on a display screen or other user interface coupled to a computer, e.g., computer 50, 50', 60, 500, 500', or 600. The displayed data may include, for example, a waveform of the evoked potential over time, a waveform of the stimulation signal eliciting the evoked potential over time, and/or quantitative characteristics of the evoked potential such as amplitude, frequency, width, slope, or latency relative to the stimulus. Display of such information in a graphical user interface may help a clinician observe and understand changes in the evoked potential over time. By comparing evoked potentials before, during, and after a stimulation session, and/or over time between stimulation sessions, clinicians can follow and monitor a patient's treatment.

At step 1612, one or more inputs are received, e.g., with the input device, to adjust the stimulation protocol. For example, based on the observed evoked potential, a clinician may wish to increase or decrease one or more parameters of the stimulus to elicit a stronger contraction, a smooth contraction, or other desired result. At step 1614, the muscle of the patient is stimulated with the adjusted stimulation protocol using, e.g., a stimulating electrode coupled to an NMES device or an inductance coil of a TMS system. The resulting signal containing an evoked potential generated by the patient's body in response to the adjusted stimulation protocol may then be recorded, processed, and displayed as described above.

The time between recording, processing and displaying the evoked potential to the time of generation of an adjusted stimulation protocol may vary according to the need. In one embodiment, the time may be short so that the stimulation protocol is adjusted in real time (or virtually real time). In another embodiment, the time may be long (hours, days, weeks or longer) so that the long term effect of the stimulation protocol can be adjusted to yield the desired physiological response.

In some embodiments, a therapeutic stimulation protocol is set by a clinician during a patient visit, and the steps of stimulating, recording, processing, displaying, and adjusting are performed during the same visit, enabling a clinician to experiment with different stimulation protocols and tweak stimulation parameters to achieve a therapeutic stimulation protocol that results in the greatest activation of the target muscle or other desired effect. In this manner, a clinician may be empowered to optimize a patient's treatment.

In other embodiments, the therapeutic stimulation protocol is set by a clinician during a patient visit, and the protocol is repeated regularly (e.g., every other day, daily, twice daily, hourly) until the patient's next visit. The evoked potentials from each stimulation session may be recorded and stored in the patient's implanted stimulating device. At the next visit, the clinician is then able to retrieve the stored evoked potential data from the device and view data indicative of the evoked potentials on a user interface to observe changes and trends. Based on the historical evoked potential data acquired and saved by the stimulation device, the clinician can determine if any adjustments are needed to the stimulation protocol and can further determine how treatment is progressing.

In a further embodiment, the system may be self-adjusting such that the stimulation protocol is adjusted automatically by the device in order to achieve the desired physiological response. The algorithm for self-adjustment may be hard wired (e.g., in the software in the system), or may be determined by the clinician (e.g., by programming certain parameters).

The system described may be used to monitor the progress of other types of rehabilitative therapy such as physiotherapy, or combination therapies such as physiotherapy used in conjunction with NMES and/or TMS for rehabilitation.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for monitoring rehabilitation of a muscle, the method comprising:
    receiving from an extracorporeal source a first input defining a first stimulation protocol, the first stimulation protocol comprising a plurality of parameters for generation of an electric current or an electric voltage;
    generating an electromagnetic field in accordance with the first stimulation protocol via a transcranial magnetic stimulation device and applying the electromagnetic field to a portion of a patient's body to cause contraction of a skeletal target muscle associated with control of the lumbar spine;
    generating a trigger signal via trigger detector communicatively coupled to the transcranial magnetic stimulation device upon generation of the electromagnetic field;
    recording a response signal generated by the patient's body in response to the first stimulation protocol via an implanted recording electrode implanted on, in, or a the skeletal target tissue, wherein the response signal is at least one of an electrical signal, a force signal, or a movement signal;
    processing the recorded response signal to produce processed signal responsive to receiving the trigger signal;
    displaying information indicative of the processed signal.

2. The method of claim 1, wherein the plurality of parameters are selected from a group of parameters consisting of: pulse amplitude, pulse width, stimulation rate, stimulation frequency, ramp timing, cycle timing, session timing, duty cycle, contacts activated, percent of total current allocated to each contact, and location of stimulation.

3. The method of claim 1, wherein the target muscle is at least one of the lumbar multifidus, the transverse abdominus, the erector spinae, the iliocostalis, and the longissimus.

4. The method of claim 1, wherein the electric current or electric voltage of the first stimulation protocol comprises a plurality of electrical pulses.

5. The method of claim 1, wherein the recorded response signal or the processed signal is transmitted wirelessly to an external receiver.

6. The method of claim 1, wherein the response signal is recorded by a surface electrode electrically coupled to the implanted recording electrode, the surface electrode attached to the patient at the head, neck, or spine, and wherein the recorded response signal is received by a processor from the surface electrode via a wired or wireless connection.

7. The method of claim 1, wherein the response signal is an electrical signal and wherein processing the recorded response signal comprises at least one of amplifying, filtering and digitizing the recorded response signal.

8. The method of claim 1, wherein processing the recorded response signal comprises taking a temporal average of the recorded response signal.

9. The method of claim 1, further comprising: receiving a second input from the extracorporeal source to adjust the first stimulation protocol; and generating an electromagnetic field in accordance with an adjusted stimulation protocol.

10. The method of claim 9, wherein processing the recorded response signal comprises synchronizing the recorded response signal with the trigger signal.

11. The method of claim 9, further comprising recording a second response signal comprising an adjusted response signal generated in response to the adjusted stimulation protocol, processing the second response signal to produce a second processed signal, and displaying information indicative of the second processed signal.

12. The method of claim 1, wherein the response signal is an evoked potential.

13. The method of claim 1, wherein information indicative of the processed signal comprises: a waveform of the processed signal, and/or one or more quantitative metrics of the processed signal selected from the group consisting of: amplitude, width, frequency, latency relative to application of the first stimulation protocol, and slope.

* * * * *